(12) United States Patent
Wang

(10) Patent No.: US 7,700,590 B2
(45) Date of Patent: Apr. 20, 2010

(54) ANTIBACTERIAL AGENTS

(75) Inventor: Guijun Wang, Metairie, LA (US)

(73) Assignee: University of New Orleans Research and Technology Foundation, Inc., New Orleans, LA (US)

(*) Notice: Subject to any disclaimer, the term of this patent is extended or adjusted under 35 U.S.C. 154(b) by 0 days.

(21) Appl. No.: 12/278,871

(22) PCT Filed: Feb. 9, 2007

(86) PCT No.: PCT/US2007/061943
§ 371 (c)(1),
(2), (4) Date: Aug. 8, 2008

(87) PCT Pub. No.: WO2007/092961
PCT Pub. Date: Aug. 16, 2007

(65) Prior Publication Data
US 2009/0048240 A1    Feb. 19, 2009

Related U.S. Application Data

(60) Provisional application No. 60/771,759, filed on Feb. 9, 2006.

(51) Int. Cl.
*C07D 263/06* (2006.01)
*C07D 265/06* (2006.01)
*A61K 31/538* (2006.01)
(52) U.S. Cl. .................. 514/228.8; 544/88; 544/96
(58) Field of Classification Search .................. 544/88, 544/96; 514/228.8
See application file for complete search history.

(56) References Cited

FOREIGN PATENT DOCUMENTS

| EP | 0928789 A1 | 7/1999 |
|---|---|---|
| WO | 03000256 A1 | 1/2003 |
| WO | 03106413 A2 | 12/2003 |
| WO | 2007039134 A1 | 4/2007 |
| WO | 2007042146 A1 | 4/2007 |

OTHER PUBLICATIONS

Wang et al. Bioorganic & Medicinal Chemistry Letters (2006), 16(8), 2177-2181.*
Barbachyn, Michael R., et al., "Oxazolidinone Structure—Activity Relationships Leading to Linezolid", Angew. Chem. Int. Ed. 2003, vol. 42, p. 2010-2023.
Bozdogan, Bulent, et al., "Oxazolidinones: Activity, Mode of Action, and Mechanism of Resistance", International Journal of Antimicrobial Agents, 2004, vol. 23, Issue 2, p. 113-119.
Brickner, Steven J., "Oxazolidinone Antibacterial Agents", Current Pharmaceutical Design, 1996, vol. 2, p. 175-194.
Chemical Abstracts Service. Igarashi, H., et al., "Derivatives of Amino Alcohols. III. Synthesis and Pharmacology of Cyclic Compounds Containing Two Hetero Atoms", Yakugaku Zasshi, 1974, vol. 94, No. 4, p. 444-451. (8 pages).
Chemical Abstracts Service, Murdock, K., "2-Oxazolidinones From an N-dealkylation Reaction of Phosgene With Dialkylaminoalkanols. Isolation and Reactivities of an N-acyl Quaternary Ammonium Intermediate", Journal of Organic Chemistry, 1968, vol. 33, No. 4, p. 1367-1371. (1 page).
Chemical Abstracts Service. Ludwig, B. J., et al., "(Aminomethyl)oxazolidinones Derived From Substituted Diamino-2-propanols", Journal of the American Chemical Society, 1954, vol. 76, p. 2891-2893. (6 pages).
Chen, Yeh-Long, et al., "Synthesis and Antibacterial Evaluation of Certain Quinolone Derivatives", Journal of Medicinal Chemistry, 2001, vol. 44, No. 14, p. 2374-2377.
Diekema, Daniel J., et al., "Oxazolidinone Antibiotics", The Lancet, 2001, vol. 358, p. 1975-1982.
Drlica, Karl, et al., "Fluoroquinolones: Action and Resistance", Current Topics in Medicinal Chemistry, 2003, vol. 3, No. 3, p. 249-282.

(Continued)

*Primary Examiner*—Kahsay T Habte
(74) *Attorney, Agent, or Firm*—McGlinchey Stafford, PLLC

(57) ABSTRACT

This invention provides compositions which are 1,3-oxazinan-2-one compounds of formulae (I) and (II), and oxazolidinone compounds of formula (III): wherein R is a hydrocarbyl group, a heterocyclic group, a hydrocarbyl group having at least one substituent, or a heterocyclic group having at least one hydrocarbyl substituent, wherein the substituent on the hydrocarbyl group or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms; and R' and R" are each independently hydrogen, an alkyl group, an aryl group, a methylaryl group, a carbonyl group, a hydrocarbylamido group, a sulfonyl group, a sulfonamoyl group, a heterocyclic group, a heterocyclic group having at least one substituent, or an aryl group or methylaryl group having at least one substituent, where the substituent on the heterocyclic group, aryl group, or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms. For the oxazolidinone compound of formula (HI), there is a proviso that when one of R' or R" is a (3-fluoro)-(4-morpholinyl)-phenyl group, the other of R' or R" is not an acetamido group.

27 Claims, 6 Drawing Sheets

OTHER PUBLICATIONS

Ella-Menye, Jean-Rene, et al. "New Synthesis of Chiral 1,3-Oxazinan-2-ones from Carbohydrate Derivatives", Journal of Organic Chemistry, 2005, vol. 70, p. 463-469.

Giacometti, Andrea, et al. "In Vitro Activity of the Histatin Derivative P-113 Against Multidrug-Resistant Pathogens Responsible for Pneumonia in Immunocompromised Patients", Antimicrobial Agents and Chemotherapy, 2005, vol. 49, No. 3, p. 1249-1252.

Higgins, P. G., et al., "Fluoroquinolones: Structure and Target Sites", Current Drug Targets, 2003, vol. 4, No. 2, p. 181-190.

Hollingsworth, Rawle I., et al., "Oxazolidinones, Antibacterial", Kirk-Othmer Encyclopedia of Chemical Technology, 2003, vol. 17, p. 728-746.

Hu, X. Eric, et al., "Discovery of (3S)-Amino-(4R)-ethylpiperidinyl Quinolones as Potent Antibacterial Agents with a Broad Spectrum of Activity and Activity Against Resistant Pathogens", Journal of Medicinal Chemistry, 2003, vol. 46, No. 17, p. 3655-3661.

Hutchinson, Douglas K., "Oxazolidinone Antibacterial Agents: A Critical Review", Current Topics in Medicinal Chemistry, 2003, vol. 3, No. 9, p. 1021-1042.

Masters, Philip a., et al., "Trimethoprim-Sulfamethoxazole Revisited", Arch. Intern. Med., 2003, vol. 163, p. 402-410.

Mitscher, Lester A., et al., "Multiple Drug Resistance", Med. Res. Rev., 1999, vol. 19, p. 477-496.

Pootoolal, Jeff, et al. "Glycopeptide Antibiotic Resistance", Annual Review of Pharmacology and Toxicology, 2002, vol. 42, p. 381-408.

Raad, Issam I., et al. "Clinical-Use-Associated Decrease in Susceptibility of a Vancomycin-Resistant Enterococcus faecium to Linezolid: a Comparison with Quinupristin-Dalfopristin", Antimicrobial Agents and Chemotherapy, 2004, vol. 48, No. 9, p. 3583-3585.

Seneci, Pierfausto, et al., "Synthesis and Antimicrobial Activity of Oxazolidin-2-ones and Related Heterocycles", Journal of the Chemical Society, Perkin Transactions 1: Organic and Bio-organic Chemistry, 1994, (16), p. 2345-2351.

Sokilde, Birgitte, et al., "Analogues of Carbacholine: Synthesis and Relationship Between Structure and Affinity For Muscarinic and Nicotinic Acetylcholine Receptors", Arch. Pharm. Pharm. Med. Chem., 1996, vol. 329, p. 95-104.

Swenson, Jana M., et al. "Optimal Inoculation Methods and Quality Control for the NCCLS Oxacillin Agar Screen Test for Detection of Oxacillin Resistance in Staphylococcus aureus", Journal of Clinical Microbiology, 2001, vol. 39, No. 10, p. 3781-3784.

Wang, Guijun, et al. "A Simple Three-Step Method for Preparing Homochiral 5-trityloxymethyl-2-oxazolidinones From Optically Active 3-hydroxy-gamma-butyrolactones", Tetrahedron: Asymmetry, 2000, vol. 11, p. 4429-4432.

Wang, Guijun, et al., "Direct Conversion of (S)-3-Hydroxy-gamma-butyrolactone to Chiral Three-Carbon Building Blocks", Journal of Organic Chemistry, 1999, vol. 64, p. 1036-1038.

Wang, Guijun, et al., "Synthesis and Antibacterial Activities of Chiral 1,3-oxazinan-2-one Derivativies", Bioorganic & Medicinal Chemistry Letters, 2006, vol. 16, p. 2177-2181.

Zhanel, George G., et al., "A Critical Review of the Fluoroquinolones Focus on Respiratory Tract Infections", Drugs, 2002, vol. 62, No. 1, p. 13-59.

\* cited by examiner

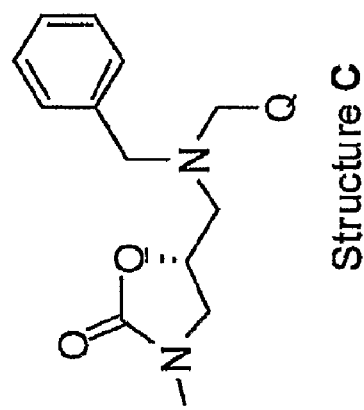
Structure C
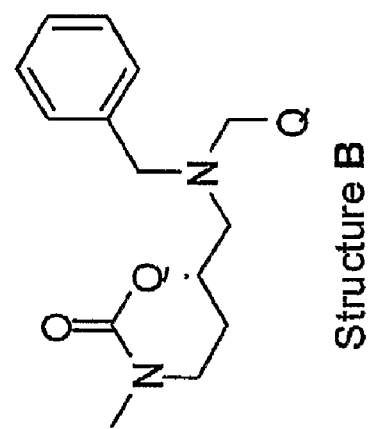
Structure B
Fig. 6
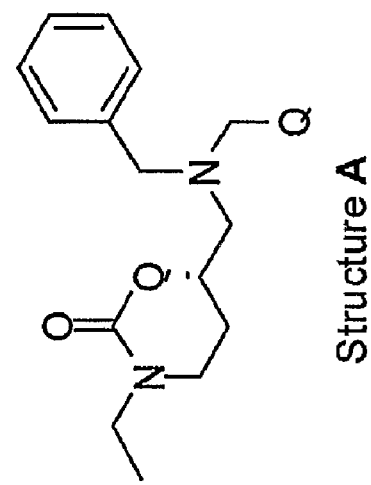
Structure A

ANTIBACTERIAL AGENTS

REFERENCE TO RELATED APPLICATIONS

This application is the National Stage of International Patent Application PCT/US2007/061943, filed on Feb. 9, 2007, which application claims priority from U.S. application Ser. No. 60/771,759, filed Feb. 9, 2006, the disclosures of which are incorporated herein by reference.

TECHNICAL FIELD

This invention relates to 1,3-oxazinan-2-ones and oxazolidinones which can be used as antibacterial agents.

BACKGROUND

Antibiotic resistance is a growing problem that threatens human health globally. Infections caused by methicillin-resistant *Staphylococcus aureus* (MRSA) and vancomycin-resistant *enterococci* (VRE) (see Pootoolal, J., et al., *Annu. Rev. Pharmacol. Toxicol.* 2002, 42, 381; and Raad, I. I., et al., *Antimicrob. Agents Chemother.* 2004, 48, 3583) are very dangerous and can be life threatening especially for patients whose immune systems have been compromised due to HIV, surgery or other illness. During the recent decades, the effort of discovering novel antibacterial agents has slowed down; in fact, oxazolidinones are the only new class of synthetic antibacterial agents over the past 30 years that possess totally new structures compared to existing antibacterial agents. See in this connection Brickner, S. J., *Curr. Pharma. Design* 1996, 2, 175; Diekema, D. J. and Jones, R. N., *Lancet* 2001, 358, 1975; Hollingsworth, R. I. and Wang, G., *Kirk-Othmer Encyclopedia of Chemical Technology*, Dec. 19, 2003; and Bozdogan, M. and Appelbaum, P. C., *Int. J. Antimicrob. Agents* 2004, 23, 113. The first compound of this class, Linezolid 1 (FIG. 1), was approved in 2000 for the treatment of multi-drug resistant bacterial infections including diseases caused by MRSA, VRE and *Streptoccus pneumoniae*. Oxazolidinones bind to the 50S subunit of the bacterial ribosome and inhibit protein synthesis at a very early stage by preventing the initiation of mRNA translation. Because they target the bacterial protein synthesis at an early stage, drug resistance was expected to be rare; however resistance to Zyvox (Linezolid) has already been reported (see Barbachyn, M. R. and Ford, C. W., *Angew. Chem. Int. Ed. Engl.* 2003, 42, 2010; and Hutchinson, D. K., *Curr. Top. Med. Chem.* 2003, 3, 1021).

Some structures of the existing small molecule antibacterial agents are shown in FIG. 1. These include Linezolid (1), Ciprofloxacin (2), Sulfonamide (3) and Chloramphenicol (4). The very general features of these agents are that they all contain aromatic and/or heterocyclic structures and they have heteroatom substituents such as halo, amino and/or hydroxyl groups. Linezolid has oxazolidinone as its core structure, which is important for its activity. Ciprofloxacin is one example of the fluoroquinolone class of antibiotics. See in this connection Higgins, P. G., et al., *Curr. Drug Targets* 2003, 4, 181; Zhanel, G. G., et al., *Drugs* 2002, 62, 13; Drlica, K. and Malik, M., *Curr. Top. Med. Chem.* 2003, 3, 249; Chen, Y.-L., et al., *J. Med. Chem.* 2001, 44, 2374; Hu, X. E., et al., *J. Med. Chem.* 2003, 46, 3655. They kill bacteria by inhibiting DNA gyrase enzyme which is essential for DNA replication. The structure of ciprofloxacin contains a fused aromatic ring with a fluorine substituent and a polar piperazine substituent. Sulfonamide contains phenyl sulfonyl phenyl amines. The sulfonamides are inhibitors of the bacterial enzymes required for the synthesis of tetrahydrofolate (see Masters, P. A., et al., *Arch. Internal Medicine* 2003, 163, 402), an essential nutrient for bacterial growth. Chloramphenicol contains substituted nitrophenol with dichloromethyl acetamido functional groups. It also inhibits bacterial protein synthesis and is a broad spectrum antibiotic for both Gram positive and Gram negative bacteria, but chloramphenicol has some serious side effects (see Mitscher, L. A., et al., *Med. Res. Rev.* 1999, 19, 477).

Many new antibacterial agents are designed based on modification of the existing structural classes; since the antibiotic assay is easy to carry out, the modes of action of the agents often are discovered after finding them active.

It would be desirable to have a novel class of compounds which shows antibacterial activity, and especially compounds that show a high level of antibacterial activity.

SUMMARY OF THE INVENTION

This invention provides novel classes of compounds containing a chiral 1,3-oxazinan-2-one or oxazolidinone as the basic core structure. These compounds are tertiary amines containing one of the core structures and two other substituents. These new classes of compounds represent new structure scaffolds which can be further optimized to give new antibacterial agents with significantly different structures compared to existing classes of antibiotics. Several of these compounds exhibit promising antibacterial activity against several types of Gram positive bacteria, including *S. aureus, E. faecalis* and *B. subtilis*. In particular, 6-{[benzyl-(3,4-dichloro-benzyl)-amino]-methyl}-3-ethyl-[1,3]oxazinan-2-one showed good activity against each of these Gram positive bacteria. The minimum inhibition concentrations of several compositions of the invention are around 10 µg/mL.

A first embodiment of this invention is a composition which is an 1,3-oxazinan-2-one compound of formula (I)

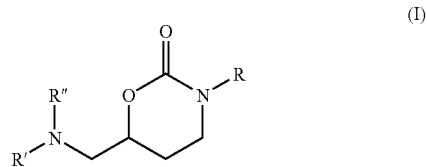

(I)

or an 1,3-oxazinan-2-one compound of formula (II)

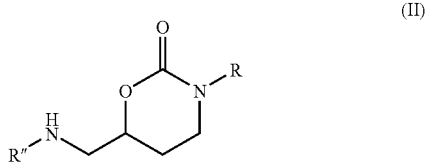

(II)

or an oxazolidinone compound of formula (III)

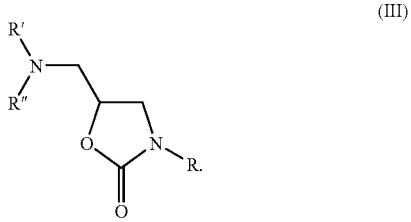

(III)

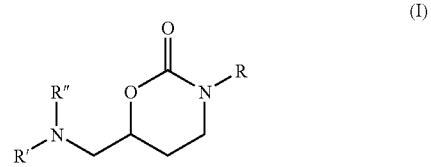

The compositions of this invention are an 1,3-oxazinan-2-one compound of formula (I)

(I)

or an 1,3-oxazinan-2-one compound of formula (II)

(II)

or an oxazolidinone compound of formula (III)

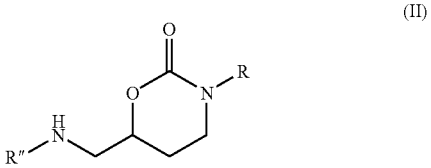

(III)

In all three formulae, R is a hydrocarbyl group (preferably an alkyl group or an aryl group), a heterocyclic group, a hydrocarbyl group having at least one substituent, or a heterocyclic group having at least one substituent, wherein the substituent on the hydrocarbyl group or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms; and R' and R" are each independently hydrogen, an alkyl group, an aryl group, a methylaryl group, a carbonyl group, a hydrocarbylamido group, a sulfonyl group, a sulfonamoyl group, a heterocyclic group, a heterocyclic group having at least one substituent, or an aryl group or methylaryl group having at least one substituent, where the substituent on the heterocyclic group, aryl group, or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms. For the oxazolidinone compound of formula (III), there is a proviso that when one of R' or R" is a (3-fluoro)-(4-morpholinyl)-phenyl group, the other of R' or R" is not an acetamido group.

These and other features, advantages and embodiments of this invention will be still further apparent from the ensuing description, drawings, and appended claims.

BRIEF DESCRIPTION OF THE DRAWINGS

FIG. 6 shows the general structures A, B, and C of compounds of this invention which have been synthesized.

DETAILED DESCRIPTION OF THE INVENTION

Figure 1:
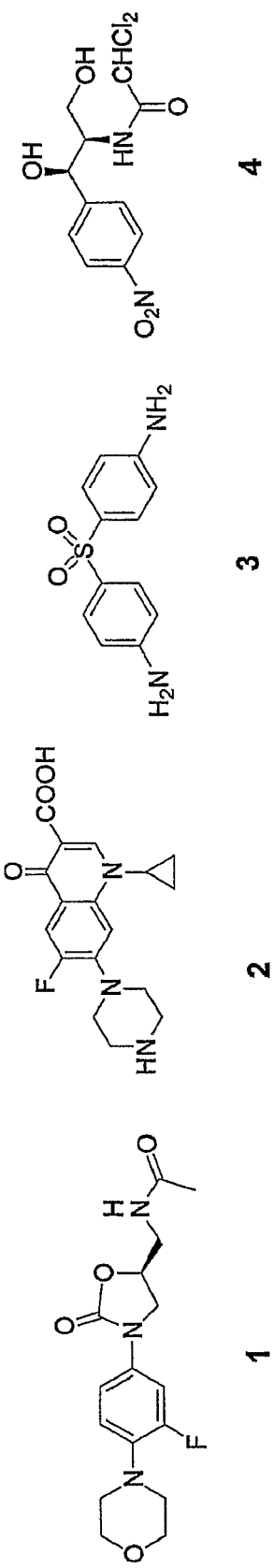
FIG. 1 shows the structures of some known synthetic antibacterial agents discussed above.

One or more compositions of this invention can be used in pharmaceutical preparations. Pharmaceutically acceptable salts of the compositions of this invention can also be used in pharmaceutical preparations. The compositions of this invention can be employed in a method for inhibiting bacterial growth, which method comprises contacting bacterial growth with one or more compositions of this invention.

In all three of the above structures, R is a hydrocarbyl group, a heterocyclic group, a hydrocarbyl group having at least one substituent, or a heterocyclic group having at least one substituent, where the substituent on the hydrocarbyl group or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms. When R is a hydrocarbyl group, it can be branched, straight-chain, cyclic, saturated or unsaturated, or aryl. Typically, the hydrocarbyl group has up to about 20 carbon atoms. Suitable hydrocarbyl groups include methyl, ethyl, n-propyl, isopropyl, cyclobutyl, sec-butyl, tert-butyl, 3-methylbutyl, pentyl, cyclopentyl, hexyl, cyclohexyl, heptyl, cycloheptyl, phenyl, naphthyl, and the like. When R is a heterocyclic group, the heterocyclic group may be saturated or unsaturated; suitable heterocyclic groups include morpholinyl groups, oxazolidinyl groups, pyrrolidinyl groups, pyridyl groups, piperazinyl groups, pyrazinyl groups, furyl groups, tetrahydrofuryl groups, pyranyl groups, tetrahydropyranyl groups, dioxanyl groups, and the like. Hydrocarbyl substituents on the heterocyclic group can be branched, straight-chain, cyclic, saturated or unsaturated, or aryl, and usually have up to about 20 carbon atoms. Suitable hydrocarbyl groups as substituents include methyl, ethyl, n-propyl, isopropyl, cyclobutyl, sec-butyl, tert-butyl, 3-methylbutyl, pentyl, cyclopentyl, hexyl, cyclohexyl, heptyl, cycloheptyl, phenyl, naphthyl, and the like.

In all three of the above structures, R' and R" are each independently hydrogen, an alkyl group, an aryl group, a methylaryl group, a carbonyl group, a hydrocarbylamido group, a sulfonyl group, a sulfonamoyl group, a heterocyclic group, a heterocyclic group having at least one substituent, or an aryl group or methylaryl group having at least one substituent, where the substituent on the heterocyclic group, aryl group, or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, with the proviso that for formula (III), when one of R' or R" is a (3-fluoro)-(4-morpholinyl)-phenyl group, the other of R' or R" is not an acetamido group.

For R' and R", the carbonyl group can be an alkyl carbonyl group or an aryl carbonyl group; the hydrocarbylamido group can be an alkylamido group or an arylamido group; the sulfonyl group can be an alkyl sulfonyl group or an aryl sulfonyl group; and the sulfonamoyl group can be an alkyl sulfonamoyl group or an aryl sulfonamoyl groups. When the group is an alkyl carbonyl group, an alkylamido group, an alkyl sulfonyl group, or an alkyl sulfonamoyl group, the alkyl portion can be branched, straight-chain, cyclic, saturated or unsaturated, or aryl. Typically, the alkyl group has up to about 20 carbon atoms. Suitable alkyl groups include methyl, ethyl, n-propyl, isopropyl, cyclobutyl, sec-butyl, tert-butyl, 3-methylbutyl, pentyl, cyclopentyl, hexyl, cyclohexyl, heptyl, cycloheptyl, phenyl, naphthyl, and the like.

Similarly, when the group is an aryl carbonyl group, an arylamido group, an aryl sulfonyl group, or an aryl sulfonamoyl group, the aryl portion of the group can be an aryl group, a methylaryl group, an aryl group or methylaryl group having at least one substituent, where the substituent on the aryl group or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms. Suitable aryl groups include phenyl, naphthyl, anthracenyl, biphenylyl, phenanthryl, and the like. Suitable methylaryl groups include benzyl, methylnaphthyl, methylanthracenyl, methylbiphenylyl, methylphenanthryl, and the like. Heterocyclic groups that can be substituents on the aryl group or methylaryl group include, but are not limited to, morpholinyl groups, oxazolidinyl groups, pyrrolidinyl groups, pyridyl groups, piperazinyl groups, pyrazinyl groups, furyl groups, tetrahydrofuryl groups, pyranyl groups, tetrahydropyranyl groups, and dioxanyl groups. Hydrocarbyl group substituents on the aryl or methylaryl group include methyl, ethyl, propyl, isopropyl, cyclobutyl, sec-butyl, tert-butyl, pentyl, cyclopentyl, hexyl, cyclohexyl, phenyl, and the like.

For R' and R", suitable aryl groups include phenyl, naphthyl, anthracenyl, biphenylyl, phenanthryl, and the like. Suitable methylaryl groups include benzyl, methylnaphthyl, methylanthracenyl, methylbiphenylyl, methylphenanthryl, and the like. Heterocyclic groups that can be substituents on the aryl group or methylaryl group include, but are not limited to, morpholinyl groups, oxazolidinyl groups, pyrrolidinyl groups, pyridyl groups, piperazinyl groups, pyrazinyl groups, furyl groups, tetrahydrofuryl groups, pyranyl groups, tetrahydropyranyl groups, and dioxanyl groups. Hydrocarbyl group substituents on the aryl or methylaryl group include methyl, ethyl, propyl, isopropyl, cyclobutyl, sec-butyl, tert-butyl, pentyl, cyclopentyl, hexyl, cyclohexyl, and the like. Benzyl, methylnaphthyl, substituted benzyl, and substituted methylnaphthyl are preferred groups for R". Preferred substituents for the substituted benzyl groups and substituted methylnaphthyl groups include methyl groups, chloro groups, and bromo groups. It is also preferred that at least one substituent is in an ortho position on the aryl or methylaryl ring.

For the 1,3-oxazinan-2-one compounds, the structure can be viewed as a tertiary amine having an 1,3-oxazinan-2-one substituent and two other substituents, R' and R", where R' and R" are as described above. Similarly, for the oxazolidinone compounds, the structure can be viewed as a tertiary amine having a oxazolidinone substituent and two other substituents, R' and R", where R' and R" are as described above.

Figure 2:
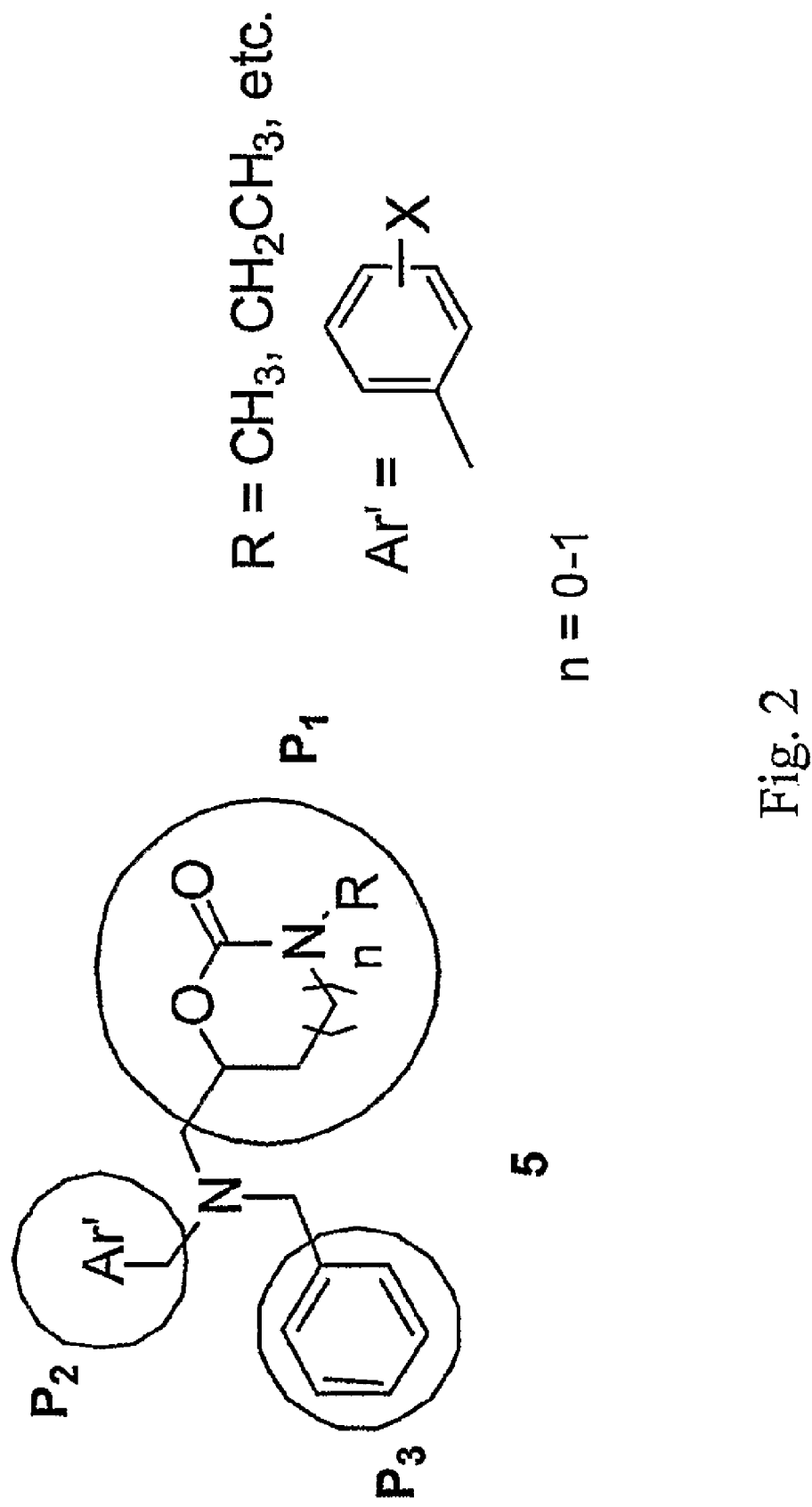
FIG. 2 shows a general structural representation of exemplary antibacterial compounds of this invention which have the 1,3-oxazinan-2-one core of formula (I).

FIG. 2 shows a general structural representation of some preferred antibacterial compounds of this application. In FIG. 2, the three sites marked $P_1$, $P_2$, and $P_3$ can be optimized to change the potency of the antibacterial agent. Site $P_1$ as shown contains a core structure which is an oxazolidinone when n=0, and is an 1,3-oxazinan-2-one when n=1. Group $P_3$ as shown in FIG. 2 is a phenyl ring, and corresponds to R' as a benzyl group. Group $P_3$ corresponds to R' of formulae (I)-(III) in the sense that when $P_3$ is a phenyl group, R' is a benzyl group. Group $P_2$, which is R" of formulae (I)-(III), as shown is a substituted benzyl moiety (a preferred moiety), where X is a cyano group, a nitro group, a fluoro group, a chloro group, a bromo group, an alkoxy group having up to 15 carbon atoms, or a hydrocarbyl group having up to 15 carbon atoms.

Referring again to FIG. 2, the structure activity relationship (SAR) of site $P_2$ can be analyzed for $P_1$ having an 1,3-oxazinan-2-one ring (n=1). The nature of substituents and their positions on the benzyl group of the compounds studied (Table 1, below) affected the antibacterial activity. Without wishing to be bound by theory, a general trend appears to be that non-polar groups are more favorable than polar groups on the aromatic ring. Also without wishing to be bound by theory, it seems that substituents in the ortho position on the $P_2$ site favor antibacterial activity as well. Ortho methyl groups and ortho halogen groups generally appear to be good substituents for antibacterial activity. Fluoro substituents frequently appear in many antibacterial drug structures. However, for the studied tertiary amine systems, chloro and bromo substituted compounds seem to be more potent than fluoro containing compounds. Compounds having a polar nitro substituent were not very active. Compounds with methylnaphthyl groups showed better antibacterial activity than those with substituted benzyl groups. When a substituted benzyl group was replaced with a pyridylmethyl group (compounds A14 and A15, Table 1, below), the antibacterial activity was either decreased or nullified. Without wishing to be bound by theory, this also suggests that it is favorable to have a nonpolar group at the site $P_2$. For site $P_1$, substituents on the 3-nitrogen of the 1,3-oxazinan-2-one ring also influence the activity. Several analogous 1,3-oxazinan-2-one compounds having ethyl groups instead of methyl groups showed greater antibacterial activity.

For the oxazolidinone series, molecules having the same $P_2$ and $P_3$ groups as the 1,3-oxazinan-2-one compounds studied indicated that the 6-membered ring 1,3-oxazinan-2-one is more potent than the 5-membered ring oxazolidinone analog. However, oxazolidinone compounds with bromo substituents on the aromatic ring ($P_2$) showed good antibacterial activity, especially for bromine in an ortho position.

From the results, we can draw several preliminary conclusions about the SAR. For systems in which site $P_2$ is aromatic, methylnaphthyl is more active than benzyl; bromo groups and methyl groups are good candidates for the substituent on the aromatic ring. The 6-membered ring 1,3-oxazinan-2-one seems to have slightly better activity than the oxazolidinone ring for the compounds tested to date.

Some of the 1,3-oxazinan-2-one compositions of the invention can be prepared in a process which comprises contacting i) an 1,3-oxazinan-2-one compound of the formula

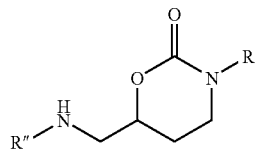

wherein R is a hydrocarbyl group, a heterocyclic group, a hydrocarbyl group having at least one substituent, or a heterocyclic group having at least one substituent, which substituent on the hydrocarbyl or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, and wherein R" is a carbonyl group, a hydrocarbylamido group, a sulfonyl group, a sulfonamoyl group, an aryl group, a methylaryl group, or an aryl group or methylaryl group having at least one substituent selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms; and ii) a compound of the formula R'L, wherein R' is a carbonyl group, a hydrocarbylamido group, a sulfonyl group, a sulfonamoyl group, an aryl group, a methylaryl group, or an aryl group or methylaryl group having at least one substituent selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms; and wherein L is a leaving group.

Preferences for R, R', and R" are as described above for the 1,3-oxazinan-2-one compositions of the invention. Suitable leaving groups L include halides, sulfonates, and the like. Suitable halide leaving groups include chloride, bromide, and iodide. Suitable sulfonate leaving groups include toluenesulfonate (tosylate), methanesulfonate (mesylate), and trifluoromethanesulfonate (triflate). L is preferably a sulfonate or a halide; when L is a halide, chloride and bromide are preferred. Other 1,3-oxazinan-2-one compositions of the invention can be prepared in a manner similar to that just described.

In the above synthesis, an inorganic base, preferably an alkali metal base, such as an alkali metal carbonate, is present. Sodium carbonate and potassium carbonate are preferred inorganic bases.

Some of the oxazolidinone compositions of the invention can be prepared in a process which comprises I) contacting an amine of the formula R'NH$_2$ and an oxazolidinone compound of the formula

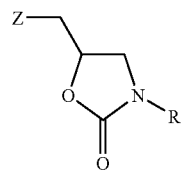

wherein R is a hydrocarbyl group, a heterocyclic group, a hydrocarbyl group having at least one substituent, or a heterocyclic group having at least one substituent, which substituent on the hydrocarbyl group or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, wherein Z is a leaving group, wherein R' is a carbonyl group, a hydrocarbylamido group, a sulfonyl group, a sulfonamoyl group, an aryl group, a methylaryl group, or an aryl group or methylaryl group having at least one substituent selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, forming an aminated product; and II) contacting at least a portion of the aminated product formed in I) with a compound of the formula R"L, R" is a carbonyl group, a hydrocarbylamido group, a sulfonyl group, a sulfonamoyl group, an aryl group, a methylaryl group, or an aryl group or methylaryl group having at least one substituent selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, to form a compound having the formula

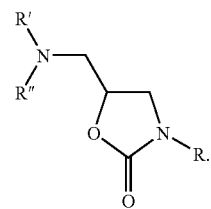

Preferences for R, R', and R" are as described above for the oxazolidinone compositions of the invention. Suitable leaving groups Z include sulfonates, halides, and the like. Suitable sulfonates include alkyl and aryl sulfonates, such as toluenesulfonate (tosylate), methanesulfonate (mesylate), and trifluoromethanesulfonate (triflate). Halide leaving groups include chloride, bromide, and iodide. For Z, sulfonates are a preferred type of leaving group, and mesylate is a preferred sulfonate leaving group. Suitable leaving groups L include halides, sulfonates, and the like. Chloride, bromide, and iodide are suitable halide leaving groups. Suitable sulfonate leaving groups include toluenesulfonate (tosylate), methanesulfonate (mesylate), and trifluoromethanesulfonate (triflate). L is preferably a halide; more preferably L is chloride or bromide. Other oxazolidinone compositions of the invention can be prepared in a manner similar to that just described.

Figure 3:
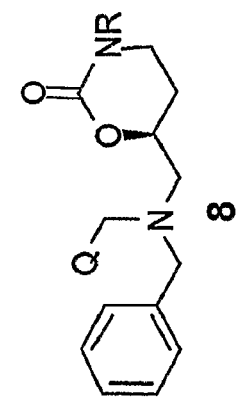
FIG. 3 shows a scheme for synthesis of 1,3-oxazinan-2-one derivatives of the invention.
Figure 3:
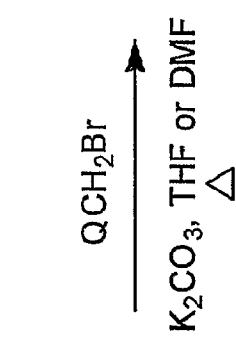
Figure 3:
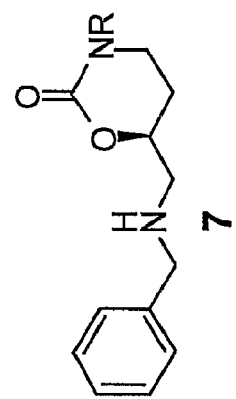
Figure 3:
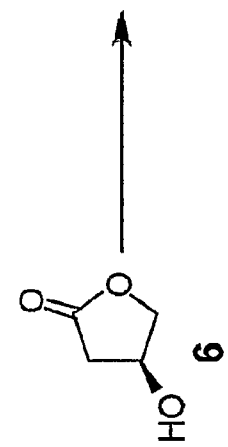

The synthesis of several compositions of the invention with the general structure 5 (see FIG. 2) were carried out, and these compositions were analyzed for their antibacterial activities. The synthesis scheme for 1,3-oxazinan-2-one ring derivatives is shown in FIG. 3. Referring now to the scheme in FIG. 3, the intermediate compound 7 was synthesized from S-3-hydroxyl γ-butyrolactone 6 as follows: optically pure (S)-3-hydroxy-butyrolactone 6 was ring-opened with an amine, quantitatively forming a dihydroxy butyramide. The dihydroxy butyramide was selectively protected with a trityl group via reaction with trityl chloride, forming a 4-trityloxy-3-hydroxy-butyramide. Reduction of the protected amide with LiAlH$_4$ gave an aminoalcohol. Contacting the aminoalcohol with carbonyl diimidazole caused cyclization, yielding a protected 1,3-oxazinan-2-one. The trityl protecting group was quantitatively removed using trifluoroacetic acid (TFA). The de-protected product, which contains one hydroxyl group, is contacted with methanesulfonate chloride; the mesylated product of this reaction is then contacted with an amine, resulting in an amino group in place of the primary hydroxy group, which product is compound 7 when the amine is benzylamine. This synthesis of compound 7 has been reported in the literature by Ella-Menye, J. R., et al., *J. Org. Chem.* 2005, 70, 463, and Wang, G. and Hollingsworth, R. I., *J. Org. Chem.* 1999, 64, 1036. The synthesis can be generalized for other amines than benzylamine, if it is desired that R" is a group other than a benzyl group, and R-3-hydroxyl γ-butyrolactone can be used as the starting material, depending on the enantiomer desired.

Referring again to the synthetic scheme in FIG. 3, alkylation of 7 with an alkyl halide in the presence of potassium carbonate in tetrahydrofuran (THF) or dimethylformamide (DMF) at 70-90° C. gave the desired product 8. This synthesis of compound 8 from compound 7 is an example of the above-described synthesis of an 1,3-oxazinan-2-one compound having both an R' and an R" group from R'L and an 1,3-oxazinan-2-one compound having the formula

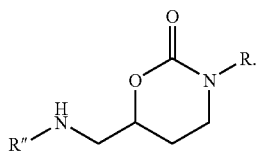

The syntheses (from compound 6 to compound 8) were carried out in solution phase and purified by flash chromatography using silica gel. R in FIG. 3 is as defined for formula (I), where R' is a benzyl group, and R" of formula (I) corresponds to Q by the addition of a methylene group to Q.

Figure 4:
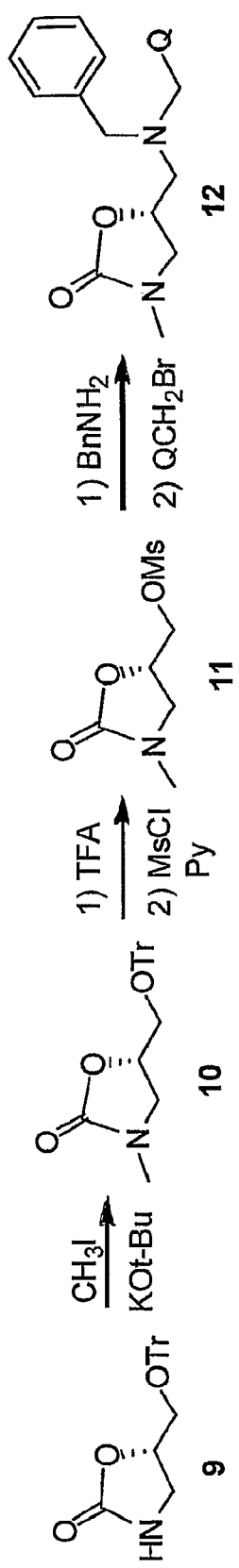
FIG. 4 shows a scheme for synthesis of oxazolidinone derivatives of the invention.

Also synthesized were compounds containing the oxazolidinone core structure. A synthesis scheme for 5-membered ring oxazolidinone derivatives is shown in FIG. 4. Referring now to the scheme in FIG. 4, the starting compound 9 was synthesized from 4-trityloxy-3-hydroxy-butyramide, which can be made as described above in the synthesis of compound 7 from compound 6. To yield compound 9 shown in FIG. 4, ammonia is used in place of the amine in the synthesis of 4-trityloxy-3-hydroxy-butyramide. The 4-trityloxy-3-hydroxy-butyramide was contacted with an aqueous sodium hypochlorite solution, and then aqueous sodium hydroxide was added, and the mixture was stirred at 55-60° C. for several hours. After a workup involving separation of the organic layer from the water layer, washing the water layer and combining the washings with the original organic layer, concentration of the organic layer, redissolution of the product, drying of the solution, and solvent removal, a solid product was obtained, which solid product is the oxazolidinone compound 9. The crude product 9 can be used without further purification. This synthesis of compound 9 has been reported in the literature by Wang, G. and Hollingsworth, R. I., *Tetrahedron Asymmetry* 2000, 11, 4429. The synthesis of compound 12 can be generalized for other amines than benzylamine, if it is desired that R" is a group other than a benzyl group, and R-3-hydroxyl γ-butyrolactone can be used as the starting material for forming the 4-trityloxy-3-hydroxy-amide, depending on the enantiomer desired. The synthesis of compound 12 from compound 11 is an example of the above-described synthesis of an oxazolidinone compound having R' and R" groups from an oxazolidinone compound having the formula

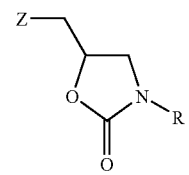

via contact with an amine of the formula R'NH$_2$, followed by contact of the aminated product with a compound of the formula R"L.

Starting from the optically pure, trityl protected oxazolidinone 9 (Tr=trityl group), the nitrogen was alkylated by treating with a base (usually an alkali metal alkoxide) and an alkyl halide to give intermediate 10. Deprotection via removal of the trityl group followed by mesylation (Ms=methanesulfonate group) in pyridine (Py) afforded 11. After displacement of the mesylate 11 with an amine (BnNH$_2$=benzylamine) and subsequent alkylation with an alkyl halide, compounds with the general structure 12 were obtained. In FIG. 4, R of formula (III) is a methyl group, and R" of formula (III) corresponds to Q by the addition of a methylene group to Q.

For the synthesis of 1,3-oxazinan-2-ones or oxazolidinones having stereochemistry opposite to that of the starting compound, the chiral center can be inverted by intramolecular $S_N2$ reaction or a Mitsunobu reaction.

Figure 5:
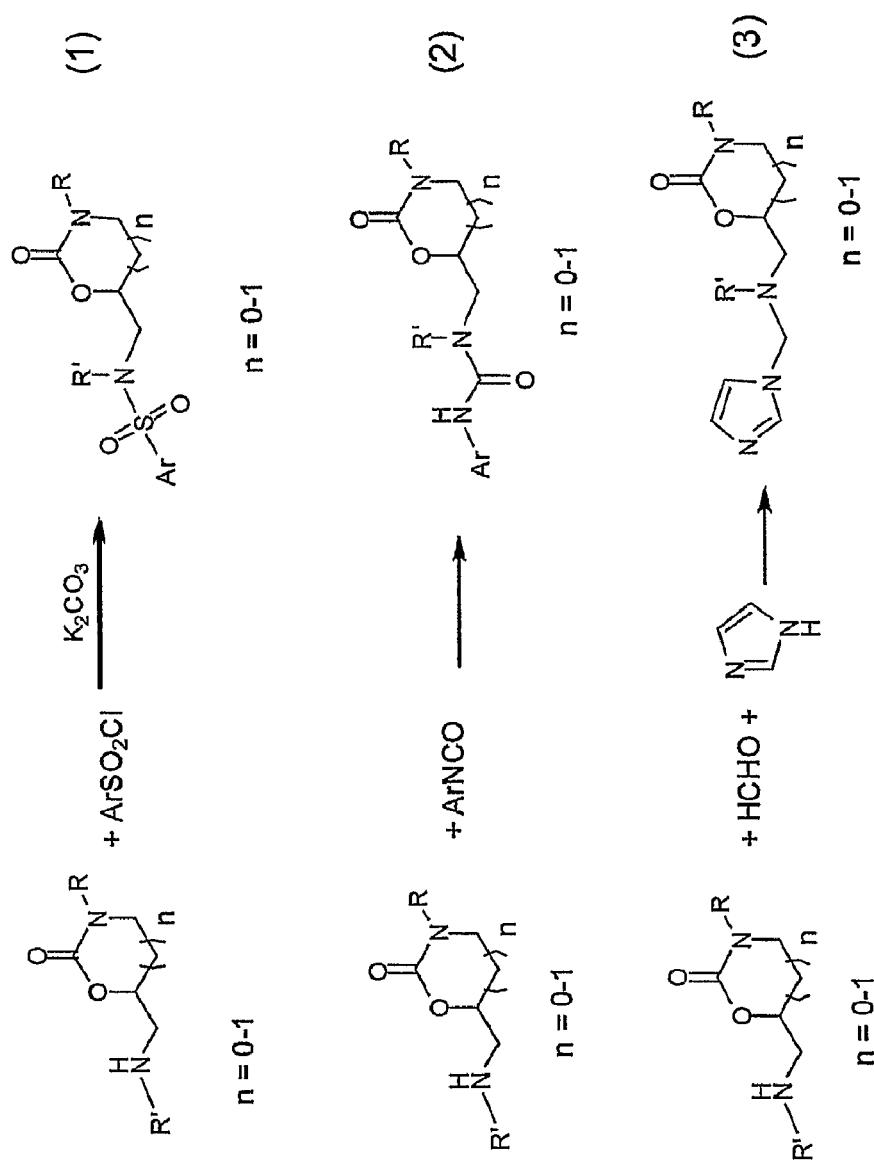
FIG. 5 shows schemes for syntheses of some 1,3-oxazinan-2-one and oxazolidinone derivatives of the invention.

FIG. 5 shows the syntheses of several 1,3-oxazinan-2-ones (n=1) and oxazolidinones (n=0). The aryl group (Ar) in Equations 1 and 2 can be an aryl group, a methylaryl group, or an aryl group or methylaryl group having at least one substituent selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms. Equation 1 shows a preparation of compounds in which R' is an aryl sulfonyl group. As shown in Equation 1, compounds in which R' is a sulfonyl group can be prepared by reacting an aryl sulfonyl chloride with the corresponding secondary amine. Alkyl sulfonyl chlorides can be used to form corresponding compounds in which R' is an alkyl sulfonyl group. As shown in Equation 2, compounds in which R' is an arylamido group can be prepared by reaction of an aryl isocyanate with the secondary amine. Alkyl isocyanates can be used to form corresponding compounds in which R' is an alkylamido group. In Equation 3, a preparation of compounds in which R' is a heterocyclic group is shown, where the heterocyclic group is an imidazolyl group. Triazole or another heterocycle can be used in place of imidazole in Equation 3.

Some compounds of the invention having general structures A, B and C, shown in FIG. 6, were synthesized. The details for the R' groups are listed in Table 1. The structures A and B are close analogs with the substituent on ring nitrogen being an ethyl group in structure A and a methyl group in structure B. Structure C contains an oxazolidinone ring instead of an 1,3-oxazinan-2-one ring. The prefixes A, B, and C in Table 1 signify what structure shown in FIG. 6 each compound has. Note that Q in FIG. 6 corresponds to R' of formulae (I) (II), and (III) by the addition of a methylene group: for example, Q=4-nitrophenyl corresponds to R'=4-nitrobenzyl.

It is worth noting that compound A13 and B9 (see Table 1, below, and FIG. 6) have some structure similarities with an antifungal drug, the tertiary amine terbinafine.

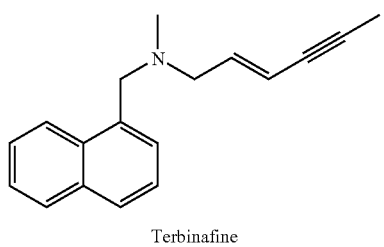

Terbinafine

All three contain a methylnaphthyl substituted tertiary amine as the general structure. Terbinafine inhibits the synthesis of ergosterol, an essential component for the fungi cell wall. It has a different mode of action compared to "azole" antifungal agents. The structural resemblance to terbinafine may indicate that the tertiary amine compositions of the invention also may have antifungal activities in addition to the observed antibacterial activities.

EXAMPLES

Procedure for the Alkylation Reaction (S)-6-(Benzylamino-methyl)-3-methyl-1,3-oxazinan-2-one (60.8 mg, 0.260 mmol) was dissolved in 5 to 10 mL of anhydrous THF. 4-nitrobenzylbromide (56.0 mg, 0.260 mmol) and potassium carbonate (72.0 mg, 0.520 mmol) were added. The solution was stirred at 60 to 70° C. for 48 h. The reaction was then cooled to room temperature and filtered on paper to remove inorganic materials. The solvent was evaporated and the residue was purified by $SiO_2$ gel chromatography using a gradient of solvent systems of Hexane/THF 9:1 to Hexane/$CH_2Cl_2$/THF 6:3:1. The product, listed as B1 in Table 1, was obtained as a brown oil (49.0 mg, 0.133 mmol). The other compounds listed in Table 1 were made in a similar manner. The general yield range was 51% to 90%. In the case of substituted benzyl chlorides, DMF is generally used as the solvent instead of THF. The alkyl chlorides usually give lower yields than alkyl bromides.

The antibacterial activities of the compounds synthesized as described above were evaluated by assay against several strains of Gram positive bacteria from the American Type Culture Collection (ATCC), *Staphylococcus aureus* 29213, *Staphylococcus aureus* 43300, *Enterococcus faecalis* 29212, and *Bacillus subtilis* PY79. The minimum inhibition concentration (MIC, μg/mL) of each compound synthesized was tested against four bacterial strains. The inhibition of bacterial growth was monitored using a standard colorimeter at 600 nm using a serial dilution at concentrations 238, 119, 59.5, 29.8, 14.9, 7.44, 3.72, 1.86, 0.93, 0.46 μg/ml. The minimum inhibition concentration (MIC) results at 50% growth inhibition for the synthesized compounds are shown in Table 1. Chloramphenicol was tested as a control, and inhibits bacteria growth ($MIC_{90}$) at 7.44, 7.44, 4.0, 2.0 μg/mL, respectively, for the four bacterial strains listed in Table 1. In Table 1, the MICs are reported as the concentrations at 50% inhibition of bacteria growth, and N stands for no inhibition.

TABLE 1

| Compound | Structure of Q | S. aureus 29213 | S. aureus 43300 | E. faecalis 29212 | B. subtilis PY79 |
| --- | --- | --- | --- | --- | --- |
| A1 | 4-nitrophenyl | N | N | 45.0 | N |
| A2 | 3-nitrophenyl | 90.0 | 22.0 | 47.0 | 108 |
| A3 | 2-nitrophenyl | 72.0 | 100 | 43.0 | 100 |
| A4 | 4-cyanophenyl | 180 | 59.5 | 12.0 | 10.0 |
| A5 | 3-cyanophenyl | 238 | N | 45.0 | 238 |
| A6 | 2-cyanophenyl | 130 | 180 | 33.0 | 160 |
| A7 | 4-fluorophenyl | 64.0 | 47.0 | 35.0 | 42.5 |
| A8 | 2,4-difluorophenyl | 45.0 | 50.5 | 59.5 | 38.0 |
| A9 | 2,6-difluorophenyl | 47.0 | 70.0 | 59.5 | 77.0 |
| A10 | 3,5-diflurophenyl | 40.0 | 45.0 | 37.0 | 43.0 |
| A11 | 3,4-dichlorophenyl | 5.60 | 6.56 | N | 5.00 |
| A12 | 2-naphthalenyl | 15.0 | N | 13.0 | 29.0 |
| A13 | 1-naphthalenyl | 10.0 | 35.0 | 7.40 | 7.60 |
| A14 | 3-pyridinyl | N | N | 238 | N |
| A15 | 2-pyridinyl | N | N | N | N |
| A16 | 3-methoxyphenyl | 90.0 | 90.0 | 80.5 | 95.0 |
| A17 | 2-methylphenyl | 22.0 | 22.5 | 8.10 | 26.0 |
| B1 | 4-nitrophenyl | 81.0 | N | 119 | 98.0 |
| B2 | 3-nitrophenyl | 138 | N | 119 | 238 |
| B3 | 2-nitrophenyl | 179 | N | 238 | 238 |
| B4 | 4-cyanophenyl | 200 | N | 238 | 238 |
| B5 | 3-cyanophenyl | 180 | 238 | 7.40 | 180 |
| B6 | 2-cyanophenyl | 166 | 180 | 59.5 | 180 |
| B7 | 4-fluorophenyl | 87.1 | 119 | 120 | 95.0 |

TABLE 1-continued

| Compound | Structure of Q | S. aureus 29213 | S. aureus 43300 | E. faecalis 29212 | B. subtilis PY79 |
|---|---|---|---|---|---|
| B8 | 2,4-difluorophenyl | 50.0 | 72.0 | 59.5 | 55.0 |
| B9 | 2-naphthalenyl | 11.5 | 13.0 | 14.9 | 12.0 |
| C1 | 4-fluorophenyl | N | N | N | N |
| C2 | 2,4-difluorophenyl | 85.0 | 119 | N | 90.0 |
| C3 | 3,4-difluorophenyl | 119 | N | N | 80.0 |
| C4 | 4-bromophenyl | 20.0 | 59.5 | N | 22.0 |
| C5 | 2-bromophenyl | 18.0 | 21.0 | 7.40 | 22.0 |

The biological assay data have shown that several compounds have moderate to potent activity against all four strains of bacteria. Some active compounds also exhibited certain strain-specificity. It is common for some bacteria strains to be resistant and others susceptible to a particular antibiotic (see Giacometti, A., et al., *Antimicrob. Agents Chemother.* 2005, 49, 1249; and Swenson, J. A., et al., *J. Clin. Microbiol.* 2001, 39, 3781). For instance, the tested strain *S. aureus* 29213 is methicillin susceptible, while *S. aureus* 43300 is methicillin resistant. The *E. faecalis* 29212 is vancomycin susceptible, another strain *E. faecalis* 51299 is vancomycin resistant. Compound A11 showed excellent activity against both strains of *S. aureus* and *B. subtilis* PY79 but no activity against *E. faecalis* 29212. Compound A12 showed promising activity against *S. aureus* 29213 but no activity against *S. aureus* 43300. Besides these two compounds, the methylphenyl derivative A17 also showed good potency, it inhibited both *S. aureus* strains, including the methicillin resistant strain, completely (greater than 90%) at concentrations of 30 µg/mL. These indicate that the more potent compounds can be developed as narrow spectrum antibiotics. This may have some advantages in controlling the spread of resistance.

In Table 1, the most potent compounds are A11, A13, A17 and B9. Their concentrations of inhibition of *S. aureus* 29213 and *B. Subtilis* 79 at 90% are shown in Table 2. Compounds A17 and C5 also inhibit over 90% growths of *E. facecalis* 29212 at concentrations of 14.9, 29.8 µg/mL respectively. The most potent compound A11 has MIC90 under 10 µg/mL, which is in the same range as chloramphenicol. These are reasonably good activities.

TABLE 2

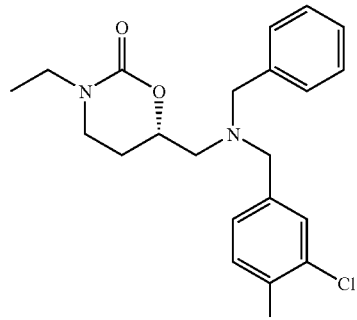
A11

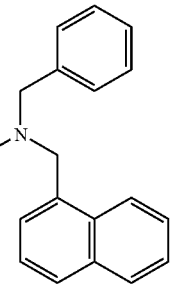
A13

| MIC$_{90}$ µg/mL | S. aureus 29213 | 9.85 | 14.9 |
|---|---|---|---|
| | B. subtilis PY79 | 7.44 | 30.0 |

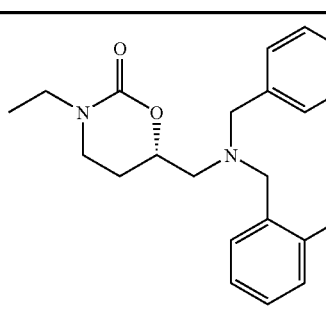
A17

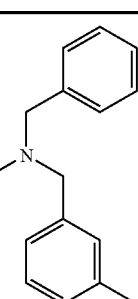
B9

TABLE 2-continued

| | | | |
|---|---|---|---|
| MIC$_{90}$ µg/mL | *S. aureus* 29213 | 29.8 | 14.9 |
| | *B. subtilis* PY79 | 59.5 | 30.0 |

The Laboratory for Advanced Applications in Glyco-Chemistry (LAAGC) at Michigan State University provided assistance in performing the antibacterial assays.

Spectroscopy data for the compounds: The $^1$H and $^{13}$C NMR spectroscopy data are listed for all of the compounds in Table 1. IR absorptions and High Resolution Mass Measurements are provided for representative compounds of each series.

Compound B1 $^1$H NMR (CDCl$_3$, 400 MHz); δ (ppm): 8.16 (d, 2H, J=8.8 Hz), 7.53 (d, 2H, J=8.8 Hz), 7.42-7.22 (m, 5H), 4.28 (m, 1H), 3.81 (d, 1H, J=14.3 Hz), 3.73 (d, 1H, J=8.8 Hz), 3.67 (d, 1H, J=14.8 Hz), 3.58 (d, 1H, J=13.2 Hz), 3.24 (dt, 1H, J=11.5, 5.5 Hz), 3.07 (m, 1H), 2.91 (s, 3H), 2.76 (dd, 1H, J=13.7, 5.5 Hz), 2.65 (dd, 1H, J=13.7, 6.0 Hz), 1.92 (m, 1H), 1.72 (m, 1H). $^{13}$C NMR (CDCl$_3$, 100 MHz); δ (ppm): 153.5, 147.2, 147.2, 138.4, 129.3, 128.8, 128.4, 127.4, 123.6, 75.5, 59.4, 58.8, 56.7, 46.0, 36.4, 25.5.

Compound B2 $^1$H NMR (CDCl$_3$, 400 MHz); δ (ppm): 8.24 (bs, 1H), 8.09 (d, 1H, J=7.8 Hz), 7.67 (d, 1H, J=7.8 Hz), 7.47 (t, 2H, J=7.8 Hz), 7.36-7.21 (m, 4H), 4.28 (m, 1H), 3.82 (d, 1H, J=14.6 Hz), 3.72 (d, 1H, J=14.6 Hz), 3.69 (d, 1H, J=13.7 Hz), 3.59 (d, 1H, J=13.7 Hz), 3.24 (dt, 1H, J=11.7, 5.9 Hz), 3.07 (m, 1H), 2.91 (s, 3H), 2.76 (dd, 1H, J=13.7, 4.9 Hz), 2.66 (dd, 1H, J=13.7, 5.9 Hz), 1.96 (m, 1H), 1.73 (m, 1H). $^{13}$C NMR (CDCl$_3$, 100 MHz); δ (ppm): 153.5, 148.3, 141.7, 138.3, 134.8, 128.3, 128.9, 128.5, 127.4, 123.3, 122.2, 75.5, 59.4, 58.7, 56.6, 46.1, 36.4, 25.5.

Compound B3 $^1$H NMR (CDCl$_3$, 400 MHz); δ (ppm): 7.76 (d, 2H, J=7.8 Hz), 7.57-7.13 (m, 7H), 4.22 (d, 1H, J=13.7 Hz), 4.13 (m, 1H), 3.76 (d, 1H, J=13.7 Hz), 3.55 (d, 1H, J=12.7 Hz), 3.39 (d, 1H, J=13.7 Hz), 3.18 (dt, 1H, J=10.7, 4.9 Hz), 2.93 (m, 1H), 2.87 (s, 3H), 2.64 (dd, 1H, J=13.7, 4.9 Hz), 2.53 (dd, 1H, J=13.7, 7.8 Hz), 1.88 (m, 1H), 1.36 (m, 1H). $^{13}$C NMR (CDCl$_3$, 100 MHz); δ (ppm): 153.7, 150.1, 137.9, 133.8, 132.3, 131.7, 129.2, 128.4, 128.2, 127.3, 124.3, 74.5, 59.7, 57.6, 56.8, 46.1, 36.4, 25.5. HRMS (m/z): calcd for C$_{20}$H$_{24}$N$_3$O$_4$ [M+H]$^+$, 370.1767; found, 370.1753. IR (CH$_2$Cl$_2$; cm$^{-1}$): 3055, 2971, 1694, 1531, 1431, 1266, 740, 700 cm$^{-1}$.

Compound B4 $^1$H NMR (CDCl$_3$, 400 MHz); δ (ppm): 7.59 (d, 2H, J=7.8 Hz), 7.47 (d, 2H, J=7.8 Hz), 7.33-7.21 (m, 5H), 4.26 (m, 1H), 3.76 (d, 1H, J=13.7 Hz), 3.68 (d, 1H, J=5.9 Hz), 3.65 (d, 1H, J=4.9 Hz), 3.57 (d, 1H, J=12.7 Hz), 3.23 (dt, 1H, J=11.7, 5.9 Hz), 3.05 (m, 1H), 2.90 (s, 3H), 2.74 (dd, 1H, J=13.7, 5.0 Hz), 2.63 (dd, 1H, J=13.7, 5.9 Hz), 1.91 (m, 1H), 1.69 (m, 1H). $^{13}$C NMR (CDCl$_3$, 100 MHz); δ (ppm): 153.5, 145.1, 138.4, 132.1, 129.3, 128.8, 128.4, 127.4, 118.8, 110.9, 75.4, 59.4, 59.1, 56.6, 46.0, 36.4, 25.4. HRMS (m/z): calcd for C$_{21}$H$_{24}$N$_3$O$_2$ [M+H]$^+$, 350.1869; found, 350.1873. IR (CH$_2$Cl$_2$; cm$^{-1}$): 3055, 2987, 1695, 1495, 1462, 1266, 744, 705 cm$^{-1}$.

Compound B5 $^1$H NMR (CDCl$_3$, 400 MHz); δ (ppm): 7.64 (bs, 1H), 7.54 (m, 1H), 7.40 (t, 1H, J=7.8 Hz), 4.25 (m, 1H), 3.73 (d, 1H, J=14.6 Hz), 3.66 (d, 1H, J=8.8 Hz), 3.62 (d, 1H, J=9.7 Hz), 3.55 (d, 1H, J=12.7 Hz), 3.23 (dt, 1H, J=10.7, 4.9 Hz), 3.05 (m, 1H), 2.90 (s, 3H), 2.67 (dd, 1H, J=13.7, 4.9 Hz), 2.63 (dd, 1H, J=13.7, 6.8 Hz), 1.92 (m, 1H), 1.70 (m, 1H). $^{13}$C NMR (CDCl$_3$, 100 MHz); δ (ppm): 153.5, 140.9, 138.4, 133.2, 132.1, 130.1, 129.1, 128.8, 128.4, 127.4, 118.9, 112.3, 75.4, 59.3, 58.7, 56.4, 45.9, 36.4, 25.5.

Compound B6 $^1$H NMR (CDCl$_3$, 400 MHz); δ (ppm): 7.59 (d, 1H, J=7.8 Hz), 7.50 (m, 2H), 7.33-7.14 (m, 6H), 4.24 (m, 1H), 3.94 (d, 1H, J=13.7 Hz), 3.71 (d, 1H, J=13.7 Hz), 3.62 (d, 1H, J=12.7 Hz), 3.49 (d, 1H, J=13.7 Hz), 3.17 (dt, 1H, J=11.7, 5.9 Hz), 2.95 (m, 1H), 2.71 (dd, 1H, J=13.7, 4.9 Hz), 2.60 (dd, 1H, J=13.7, 6.8 Hz), 1.98 (m, 1H), 1.50 (m, 1H). $^{13}$C NMR (CDCl$_3$, 100 MHz); δ (ppm): 153.4, 142.7, 138.1, 132.9, 132.4, 130.3, 128.8, 128.1, 127.7, 127.1, 117.8, 112.5, 74.7, 59.0, 58.1, 56.6, 45.8, 36.1, 25.4. HRMS (m/z): calcd for C$_{21}$H$_{24}$N$_3$O$_2$ [M+H]$^+$, 350.1869; found, 350.1872. IR (CH$_2$Cl$_2$; cm$^{-1}$): 3056, 2937, 1694, 1496, 1450, 1266, 1133, 1077, 738, 701 cm$^{-1}$.

Compound B7 $^1$H NMR (CDCl$_3$, 400 MHz); δ (ppm): 7.42-7.18 (m, 7H), 6.98 (t, 2H, J=7.8 Hz), 4.20 (m, 1H), 3.68 (d, 1H, J=5.9 Hz), 3.65 (d, 1H, J=5.9 Hz), 3.54 (d, 1H, J=5.9 Hz), 3.51 (d, 1H, J=5.9 Hz), 3.17 (dt, 1H, J=11.7, 5.9 Hz), 2.99 (m, 1H), 2.71 (dd, 1H, J=12.7, 4.9 Hz), 2.61 (dd, 1H, J=13.7, 6.8 Hz), 1.95 (m, 1H), 1.65 (m, 1H). $^{13}$C NMR (CDCl$_3$, 100 MHz); δ (ppm): 162.0 (d, C$_4$—F, $^1$J=247.2 Hz), 153.6, 138.9, 134.8, 130.4 (d, C$_2$—F, C$_6$—F, $^3$J=9.2 Hz), 128.8, 128.3, 127.2, 115.2 (d, C$_3$—F, C$_5$—F, $^2$J=21.2 Hz), 75.3, 59.4, 58.7, 56.2, 45.9, 36.4, 25.4.

Compound B8 $^1$H NMR (CDCl$_3$, 400 MHz); δ (ppm): 7.40-7.20 (m, 6H), 6.80 (m, 2H), 4.22 (m, 1H), 3.72 (d, 1H, J=13.7 Hz), 3.64 (d, 1H, J=16.6 Hz), 3.60 (d, 1H, J=13.7 Hz), 3.54 (d, 1H, J=13.7 Hz), 3.19 (dt, 1H, J=11.7, 5.9 Hz), 3.00 (m, 1H), 2.89 (s, 3H), 2.73 (dd, 1H, J=13.7, 4.9 Hz), 2.60 (dd, 1H, J=13.7, 7.8 Hz), 1.95 (m, 1H), 1.62 (m, 1H). $^{13}$C NMR (CDCl$_3$, 100 MHz); δ (ppm): 162.2 (dd, C$_4$—F, $^1$J=247.2 Hz, $^3$J=12.2 Hz), 161.5 (dd, C$_2$—F, $^1$J=247.2 Hz, $^3$J=9.2 Hz), 153.5, 138.7, 132.3 (t, C$_6$—F, $^3$J=9.2 Hz), 128.7, 128.1, 127.1, 121.7 (d, C$_1$—F, $^2$J=15.3 Hz), 111.1 (d, C$_5$—F, 2J=21.4 Hz), 103.7 (t, C$_3$—F, $^2$J=24.4 Hz), 75.3, 59.2, 56.2, 51.9, 45.9, 36.3, 25.2. HRMS (m/z): calcd for C$_{20}$H$_{23}$N$_2$O$_2$F$_2$ [M+H]$^+$, 361.1728; found, 361.1736. IR (CH$_2$Cl$_2$; cm$^{-1}$): 3055, 2985, 1694, 1504, 1438, 1266, 1137, 740, 705 cm$^{-1}$.

Compound B9 $^1$H NMR (CDCl$_3$, 400 MHz); δ (ppm): 7.91-7.21 (m, 12H), 4.23 (m, 1H), 3.85 (d, 1H, J=13.7 Hz), 3.85 (d, 1H, J=12.7 Hz), 3.75 (d, 1H, J=14.6 Hz), 3.70 (d, 1H, J=13.7 Hz), 3.60 (d, 1H, J=13.7 Hz), 3.13 (dt, 1H, 11.7, 5.9 Hz), 2.94 (m, 1H), 2.85 (s, 3H), 2.78 (dd, 1H, J=13.7, 4.9 Hz), 2.68 (dd, 1H, J=13.7, 7.8 Hz), 1.98 (m, 1H), 1.65 (m, 1H). $^{13}$C NMR (CDCl$_3$, 100 MHz); δ (ppm): 153.6, 139.1, 136.6, 133.1, 132.7, 128.9, 128.3, 127.9, 127.0, 125.9, 125.6, 75.4, 59.8, 59.6, 56.3, 45.9, 36.4, 25.4. HRMS (m/z): calcd for C$_{24}$H$_{27}$N$_2$O$_2$ [M+H]$^+$, 375.2073; found, 375.2077. IR (CH$_2$Cl$_2$; cm$^{-1}$): 3055, 2992, 2930, 1694, 1496, 1446, 1266, 1132, 1076, 740, 705 cm$^{-1}$.

Compound A1 $^1$H NMR (CDCl$_3$, 400 MHz); δ (ppm): 8.15 (d, 2H, J=8.8 Hz), 7.53 (d, 2H, J=8.8 Hz), 7.31-7.21 (m, 5H), 4.28 (m, 1H), 3.81 (d, 1H, J=14.6 Hz), 3.71 (d, 1H, J=14.6 Hz), 3.68 (d, 1H, J=12.7 Hz), 3.57 (d, 1H, J=12.7 Hz), 3.30 (q, 2H, J=14.6, 6.8 Hz), 3.22 (dt, 1H, J=11.2, 4.9 Hz), 3.08 (m, 1H), 2.75 (dd, 1H, J=13.7, 5.9 Hz), 2.64 (dd, 1H, J=13.7, 5.9 Hz), 1.95 (m, 1H), 1.69 (m, 1H), 1.08 (t, 3H, J=6.8 Hz). $^{13}$C NMR (CDCl$_3$, 100 MHz); δ (ppm): 152.9, 147.3, 138.4, 129.4, 128.8, 128.4, 127.4, 123.5, 75.3, 59.4, 58.7, 56.7, 43.9, 43.3, 25.5, 12.1.

Compound A2 $^1$H NMR (CDCl$_3$, 400 MHz); δ (ppm): 8.24 (s, 1H), 8.09 (d, 1H, J=7.8 Hz), 7.67 (d, 1H, J=7.8 Hz), 7.47

(t, 1H, J=7.8 Hz), 7.33-7.23 (m, 5H), 4.28 (m, 1H), 3.82 (d, 1H, J=13.7 Hz), 3.71 (d, 2H, J=3.9 Hz), 3.68 (d, 1H, J=3.9 Hz), 3.57 (d, 1H, J=13.7 Hz), 3.31 (q, 2H, J=14.6, 6.8 Hz), 3.22 (dt, 1H, J=11.7, 4.9 Hz), 3.08 (m, 1H), 2.76 (dd, 1H, J=13.7, 5.9 Hz), 2.66 (dd, 1H, J=13.7, 6.8 Hz), 1.99 (m, 1H), 1.69 (m, 1H), 1.09 (t, 3H, J=7.8 Hz). $^{13}$C NMR (CDCl$_3$, 100 MHz); δ (ppm): 152.9, 148.3, 141.6, 138.3, 134.8, 129.2, 128.8, 128.4, 127.4, 123.3, 122.2, 75.3, 59.3, 58.6, 56.5, 43.9, 43.3, 25.5, 12.0. HRMS (m/z): calcd for $C_{21}H_{26}N_3O_4$ [M+H]$^+$, 384.1923; found, 384.1904. IR (CH$_2$Cl$_2$; cm$^{-1}$): 3046, 2977, 1685, 1415, 1262, 735, 694 cm$^{-1}$.

Compound A3 $^1$H NMR (CDCl$_3$, 400 MHz); δ (ppm): 7.76 (d, 1H, J=8.8 Hz), 7.53 (m, 2H), 7.40 (t, 1H, J=6.8 Hz), 7.32-7.14 (m, 5H), 4.23 (d, 1H, J=13.7 Hz), 4.13 (m, 1H), 3.75 (d, 1H, J=14.6 Hz), 3.56 (d, 1H, J=13.7 Hz), 3.38 (d, 1H, J=12.7 Hz), 3.28 (m, 2H), 3.15 (dt, 1H, J=11.7, 4.9 Hz), 2.96 (m, 1H), 2.64 (dd, 1H, J=13.7, 4.9 Hz), 2.53 (dd, 1H, J=12.7, 7.8 Hz), 1.90 (m, 1H), 1.36 (m, 1H), 1.06 (t, 3H, J=7.8 Hz). $^{13}$C NMR (CDCl$_3$, 100 MHz); δ (ppm): 153.1, 150.1, 138.0, 133.8, 132.3, 131.8, 129.2, 128.3, 127.3, 124.4, 74.3, 59.6, 57.6, 56.8, 43.9, 43.3, 25.5, 12.1.

Compound A4 $^1$H NMR (CDCl$_3$, 400 MHz); δ (ppm): 7.59 (d, 2H, J=7.8 Hz), 7.46 (d, 2H, J=7.8 Hz), 7.33-7.23 (m, 5H), 4.25 (m, 1H), 3.77 (d, 1H, J=14.6 Hz), 3.68 (d, 1H, J=5.9 Hz), 3.64 (d, 1H, J=5.9 Hz), 3.55 (d, 1H, J=13.7 Hz), 3.30 (q, 2H, J=13.7, 6.8 Hz), 3.20 (dt, 1H, J=11.7, 5.9 Hz), 3.06 (m, 1H), 2.73 (dd, 1H, J=13.7, 5.9 Hz), 2.62 (dd, 1H, J=13.7, 5.9 Hz), 1.94 (m, 1H), 1.66 (m, 1H), 1.08 (t, 3H, J=6.8 Hz). $^{13}$C NMR (CDCl$_3$, 100 MHz); δ (ppm): 152.9, 145.1, 138.4, 132.1, 129.4, 128.8, 128.4, 127.4, 118.8, 110.9, 75.2, 59.4, 59.1, 56.6, 43.9, 43.2, 25.5, 12.1.

Compound A5 $^1$H NMR (CDCl$_3$, 400 MHz); δ (ppm): 7.64 (bs, 1H), 7.57 (d, 1H, J=7.8 Hz), 7.52 (d, 1H, J=6.8 Hz), 7.40 (t, 1H, J=7.8 Hz), 7.33-7.23 (m, 5H), 4.25 (m, 1H), 3.74 (d, 1H, J=14.6 Hz), 3.67 (d, 1H, J=13.7 Hz), 3.61 (d, 1H, J=13.7 Hz), 3.53 (d, 1H, J=13.7 Hz), 3.30 (q, 2H, J=14.6, 7.8 Hz), 3.21 (dt, 1H, J=11.7, 59 Hz), 3.07 (m, 1H), 2.73 (dd, 1H, J=13.7, 5.9 Hz), 2.62 (dd, 1H, J=13.7, 6.8 Hz), 1.95 (m, 1H), 1.68 (m, 1H), 1.08 (t, 3H, J=7.8 Hz). $^{13}$C NMR (CDCl$_3$, 100 MHz); δ (ppm): 152.9, 141.0, 138.4, 133.3, 132.1, 130.8, 129.1, 128.8, 128.4, 127.4, 118.9, 112.4, 75.2, 59.4, 58.7, 56.5, 43.9, 43.3, 25.5, 12.01.

Compound A6 $^1$H NMR (CDCl$_3$, 400 MHz); δ (ppm): 7.64 (D, 1H, J=7.8 Hz), 7.53 (m, 2H, J=4.9 Hz), 7.34 (m, 1H), 7.30-7.19 (m, 5H), 4.27 (m, 1H), 3.99 (d, 1H, J=13.7 Hz), 3.73 (d, 1H, J=13.7 Hz), 3.67 (d, 1H, J=13.7 Hz), 3.51 (d, 1H, J=13.7 Hz), 3.28 (q, 2H, J=14.6, 6.8 Hz), 3.17 (dt, 1H, J=11.7, 5.9 Hz), 2.99 (m, 1H), 2.75 (dd, 1H, J=13.7, 4.9 Hz), 2.63 (dd, 1H, J=13.7, 6.8 Hz), 2.05 (m, 1H), 1.51 (m, 1H), 1.06 (t, 3H, J=6.8 Hz). $^{13}$C NMR (CDCl$_3$, 100 MHz); δ (ppm): 152.9, 142.9, 138.3, 133.3, 132.6, 130.6, 129.1, 128.3, 127.8, 127.3, 118.0, 112.8, 74.7, 59.3, 58.4, 56.8, 43.8, 43.2, 25.6, 12.0. HRMS (m/z): calcd for $C_{22}H_{26}N_3O_2$ [M+H]$^+$, 364.2025; found, 364.2013. IR (CH$_2$Cl$_2$; cm$^{-1}$): 3054, 2986, 1689, 1454, 740, 705 cm$^{-1}$.

Compound A7 $^1$H NMR (CDCl$_3$, 400 MHz); δ (ppm): 7.33-7.21 (m, 6H), 6.98 (t, 2H, J=8.8 Hz), 4.20 (m, 1H), 3.69 (d, 1H, J=13.7), 3.66 (d, 1H, J=6.8 Hz), 3.52 (d, 1H, J=13.7 Hz), 3.49 (d, 1H, J=6.8 Hz), 3.28 (q, 2H, J=14.6, 6.8 Hz), 3.14 (dt, 1H, J=10.7, 4.9 Hz), 3.00 (m, 1H), 2.70 (dd, 1H, J=13.7, 4.9 Hz), 2.60 (dd, 1H, J=13.7, 7.8 Hz), 1.97 (m, 1H), 1.62 (m, 1H), 1.06 (t, 3H, J=6.8 Hz). $^{13}$C NMR (CDCl$_3$, 100 MHz); δ (ppm): 162.2 (d, $C_4$—F, $^1$J=244.1 Hz), 152.9, 138.9, 134.8, 130.6 (d, $C_2$—F, $C_6$—F, $^3$J=9.2 Hz), 128.8, 128.3, 127.1, 115.3 (d, $C_3$—F, $C_5$—F, 2J=21.4 Hz), 75.1, 59.4, 58.7, 56.1, 43.8, 43.1, 25.3, 12.0. HRMS (m/z): calcd for $C_{21}H_{26}N_2O_2F$ [M+H]$^+$, 357.1978; found, 357.1982. IR (CH$_2$Cl$_2$; cm$^{-1}$): 3054, 2983, 1690, 1446, 1266, 739, 700 cm$^{-1}$.

Compound A8 $^1$H NMR (CDCl$_3$, 400 MHz); δ (ppm): 7.37-7.19 (m, 6H), 6.83 (t, 1H, J=7.8 Hz), 6.76 (t, 1H, J=8.8 Hz), 4.22 (m, 1H), 3.72 (d, 1H, J=13.7 Hz), 3.68 (d, 1H, J=13.7 Hz), 3.59 (d, 1H, J=13.7 Hz), 3.51 (d, 1H, J=13.7 Hz), 3.29 (q, 2H, J=14.6, 7.8 Hz), 3.16 (dt, 1H, J=11.7, 5.9 Hz), 3.01 (m, 1H), 2.72 (dd, 1H, J=13.7, 4.9 Hz), 2.59 (dd, 1H, J=13.7, 7.8 Hz), 1.97 (m, 1H), 1.60 (m, 1H), 1.07 (t, 3H, J=6.8 Hz). $^{13}$C NMR (CDCl$_3$, 100 MHz); δ (ppm): 162.4 (dd, $C_4$—F, $^1$J=250.2 Hz, $^3$J=12.2 Hz), 161.6 (dd, $C_2$—F, $^1$J=247.2 Hz, $^3$J=12.2 Hz), 152.9, 138.8, 132.4 (t, $C_6$—F, $^3$J=9.2 Hz), 128.8, 128.2, 127.2, 121.9 (d, $C_1$—F, 2J=15.3 Hz), 111.3 (d, $C_5$—F, $^2$J=21.4 Hz), 103.9 (t, $C_3$—F, $^2$J=24.4 Hz), 75.1, 59.3, 56.2, 51.9, 43.9, 43.2, 25.3, 12.0.

Compound A9 $^1$H NMR (CDCl$_3$, 400 MHz); δ (ppm): 7.28-7.18 (m, 6H), 6.86 (t, 2H, J=7.8 Hz), 4.23 (m, 1H), 3.80 (d, 1H, J=13.7 Hz), 3.73 (d, 1H, J=6.8 Hz), 3.70 (d, 1H, J=6.8 Hz), 3.50 (d, 1H, J=13.7 Hz), 3.28 (m, 2H), 3.12 (dt, 1H, J=11.7, 5.9 Hz), 2.96 (m, 1H), 2.72 (dd, 1H, J=13.7, 4.9 Hz), 2.56 (dd, 1H, J=13.7, 8.8 Hz), 2.02 (m, 1H), 1.54 (m, 1H), 1.06 (t, 3H, J=6.8 Hz). $^{13}$C NMR (CDCl$_3$, 100 MHz); δ (ppm): 162.3 (dd, $C_2$—F, $C_6$—F, $^1$J=250.2 Hz, $^3$J=9.2 Hz), 153.1, 139.0, 129.6 (t, $C_4$—F, $^3$J=12.2 Hz), 129.2, 128.1, 127.1, 114.5 (t, $C_1$—F, $^2$J=18.3 Hz), 111.5 (dd, $C_3$—F, $C_5$—F, $^2$J=18.3 Hz, $^4$J=6.1 Hz), 74.9, 59.5, 55.8, 46.4, 43.9, 43.2, 25.1, 12.0. HRMS (m/z): calcd for $C_{21}H_{25}N_2O_2F_2$ [M+H]$^+$, 375.1884; found, 375.1883. IR (CH$_2$Cl$_2$; cm$^{-1}$): 3054, 2987, 1687, 1471, 740, 705 cm$^{-1}$.

Compound A10 $^1$H NMR (CDCl$_3$, 400 MHz); δ (ppm): 7.33-7.21 (m, 5H), 6.88 (d, 2H, J=6.8 Hz), 6.67 (t, 1H, J=8.8 Hz), 4.24 (m, 1H), 3.71 (d, 1H, J=3.9 Hz), 3.68 (d, 1H, J=3.9 Hz), 3.56 (d, 1H, J=6.8 Hz), 3.53 (d, 1H, J=6.8 Hz), 3.31 (q, 2H, J=13.7, 6.8 Hz), 3.21 (dt, 1H, J=11.7, 5.9 Hz), 3.07 (m, 1H), 2.73 (dd, 1H, J=13.7, 4.8 Hz), 2.63 (dd, 1H, J=13.7, 7.8 Hz), 1.99 (m, 1H), 1.70 (m, 1H), 1.09 (t, 3H, J=6.8 Hz). $^{13}$C NMR (CDCl$_3$, 100 MHz); δ (ppm): 163.3 (dd, $C_3$—F, $C_5$—F, $^1$J=250.2 Hz, $^3$J=12.2 Hz), 152.9, 143.9 (t, $C_1$—F, $^3$J=9.2 Hz), 138.5, 128.8, 128.4, 127.3, 111.4 (dd, $C_2$—F, $C_6$—F, $^2$J=18.3 Hz, $^4$J=6.1 Hz), 102.7 (t, $C_4$—F, $^2$J=24.4 Hz), 75.3, 59.4, 58.8, 56.4, 43.9, 43.3, 25.5, 12.1.

Compound A11 $^1$H NMR (CDCl$_3$, 400 MHz); δ (ppm): 7.42 (bs, 1H), 7.36 (d, 1H, J=7.8 Hz), 7.33-7.23 (m, 5H), 7.17 (d, 1H, J=7.8 Hz), 4.23 (m, 1H), 3.68 (d, 1H, J=1.9 Hz), 3.65 (d, 1H, J=1.9 Hz), 3.54 (d, 1H, J=2.9 Hz), 3.50 (d, 1H, J=2.9 Hz), 3.30 (q, 2H, J=14.6, 6.8 Hz), 3.19 (dt, 1H, J=11.7, 4.9 Hz), 3.05 (m, 1H), 2.71 (dd, 1H, J=13.7, 5.9 Hz), 2.60 (dd, 1H, J=13.7, 6.8 Hz), 1.96 (m, 1H), 1.67 (m, 1H), 1.08 (t, 3H, J=6.8 Hz). $^{13}$C NMR (CDCl$_3$, 100 MHz); δ (ppm): 152.9, 139.7, 138.5, 132.3, 130.9, 130.5, 130.2, 128.8, 128.4, 128.1, 127.3, 75.2, 59.3, 58.3, 56.3, 43.9, 43.2, 25.5, 12.1. HRMS (m/z): calcd for $C_{21}H_{25}N_2O_2Cl_2$ [M+H]$^+$, 407.1293; found, 407.1292. IR (CH$_2$Cl$_2$; cm$^{-1}$): 3048, 2969, 1690, 1462, 1266, 740, 703 cm$^{-1}$.

Compound A12 $^1$H NMR (CDCl$_3$, 400 MHz); δ (ppm): 7.79 (d, 3H, J=7.7 Hz), 7.72 (s, 1H), 7.50-7.42 (m, 3H), 7.37-7.22 (m, 5H), 4.23 (m, 1H), 3.87 (d, 1H, J=13.7 Hz), 3.76 (d, 1H, J=13.7 Hz), 3.67 (d, 1H, J=13.7 Hz), 3.57 (d, 1H, J=13.7 Hz), 3.25 (q, 2H, J=14.3, 7.1 Hz), 3.09 (dt, 1H, J=10.9, 4.9 Hz), 2.94 (m, 1H), 2.77 (dd, 1H, J=13.7, 4.9 Hz), 2.67 (dd, 1H, J=13.7, 7.7 Hz), 1.99 (m, 1H), 1.63 (m, 1H), 1.02 (t, 3H, J=7.1 Hz). HRMS (m/z): calcd for $C_{25}H_{29}N_2O_2$ [M+H]$^+$, 389.2229; found, 3891.2236. IR (CH$_2$Cl$_2$; cm$^{-1}$): 3054, 2987, 1688, 1438, 1266, 740, 705 cm$^{-1}$.

Compound A13 $^1$H NMR (CDCl$_3$, 400 MHz); δ (ppm): 8.07 (m, 1H), 7.78 (m, 2H), 7.48-7.24 (m, 9H), 4.15 (d, 1H, J=12.7 Hz), 4.03 (m, 1H), 3.92 (d, 1H, J=12.7 Hz), 3.82 (d, 1H, J=13.7 Hz), 3.62 (d, 1H, J=13.7 Hz), 3.20 (m, 2H), 2.86-2.61 (m, 4H), 1.69 (m, 1H), 1.32 (m, 1H), 0.99 (t, 3H, J=6.8 Hz). $^{13}$C NMR (CDCl$_3$, 100 MHz); δ (ppm): 152.8, 138.7, 134.5, 133.7, 132.1, 129.3, 128.3, 128.1, 128.0, 127.7, 127.2, 125.5, 125.4, 125.1, 124.6, 74.9, 60.6, 58.3, 56.0, 43.7, 42.7, 24.9, 11.9. HRMS (m/z): calcd for C$_{25}$H$_{29}$N$_2$O$_2$ [M+H]$^+$, 389.2229; found, 389.2236. IR (CH$_2$Cl$_2$; cm$^{-1}$): 3046, 2977, 1692, 1465, 1292, 766, 706 cm$^{-1}$.

Compound A14 $^1$H NMR (CDCl$_3$, 400 MHz); δ (ppm): 8.57 (bs, 1H), 7.73 (d, 1H, J=7.8 Hz), 7.34-7.21 (m, 6H), 4.27 (m, 1H), 3.77 (d, 1H, J=14.6 Hz), 3.72 (d, 1H, J=14.6 Hz), 3.63 (d, 1H, J=14.6 Hz), 3.58 (d, 1H, J=14.6 Hz), 3.30 (q, 2H, J=13.7, 6.8 Hz), 3.20 (dt, 1H, J=11.7, 5.9 Hz), 3.04 (m, 1H), 2.75 (dd, 1H, J=13.7, 4.9 Hz), 2.65 (dd, 1H, J=13.7, 6.8 Hz), 1.96 (m, 1H), 1.66 (m, 1H), 1.08 (t, 3H, J=6.8 Hz). $^{13}$C NMR (CDCl$_3$, 100 MHz); δ (ppm): 153.0, 139.1, 136.7, 133.2, 132.7, 128.9, 128.3, 127.9, 127.7, 127.6, 127.1, 126.0, 125.6, 75.2, 59.8, 56.2, 43.9, 43.1, 25.3, 12.0. HRMS (m/z): calcd for C$_{20}$H$_{26}$N$_3$O$_2$ [M+H]$^+$, 340.2025; found, 340.2025. IR (CH$_2$Cl$_2$; cm$^{-1}$): 3054, 2987, 1692, 1422, 1266, 740, 705 cm$^{-1}$.

Compound A15 $^1$H NMR (CDCl$_3$, 400 MHz); δ (ppm): 8.51 (d, 1H, J=4.9 Hz), 7.65 (t, 1H, J=6.8 Hz), 7.47 (d, 1H, J=6.8 Hz), 7.35-7.21 (m, 5H), 7.15 (t, 1H, J=5.9 Hz), 4.27 (m, 1H), 3.86 (d, 1H, J=14.6 Hz), 3.77 (d, 1H, J=5.9 Hz), 3.74 (d, 1H, J=5.9 Hz), 3.64 (d, 1H, J=14.6 Hz), 3.30 (q, 2H, J=13.7, 6.8 Hz), 3.18 (dt, 1H, J=11.7, 5.9 Hz), 3.04 (m, 1H), 2.82 (dd, 1H, J=13.7, 5.9 Hz), 2.67 (dd, 1H, J=13.7, 6.8 Hz), 2.00 (m, 1H), 1.67 (m, 1H), 1.07 (t, 3H, J=6.8 Hz). $^{13}$C NMR (CDCl$_3$, 100 MHz); δ (ppm): 159.4, 153.1, 149.0, 138.9, 136.4, 128.9, 128.3, 127.2, 123.2, 122.1, 75.2, 61.1, 59.8, 56.7, 43.9, 43.3, 25.5, 12.1.

Compound A16 $^1$H NMR (CDCl$_3$, 400 MHz); δ (ppm): 7.33-7.18 (m, 6H), 6.90 (d, 2H, J=6.8 Hz), 6.76 (d, 1H, J=7.8 Hz), 4.20 (m, 1H), 3.78 (s, 3H), 3.69 (d, 1H, J=13.7 Hz), 3.67 (d, 1H, J=8.8 Hz), 3.52 (d, 1H, J=13.7 Hz), 3.49 (d, 1H, J=7.8 Hz), 3.27 (q, 2H, J=9.8, 6.8 Hz), 3.12 (dt, 1H, J=10.7, 4.9 Hz), 2.98 (m, 1H), 2.71 (dd, 1H, J=13.7, 4.9 Hz), 2.61 (dd, 1H, J=12.7, 7.8 Hz), 2.01 (m, 1H), 1.64 (m, 1H), 1.05 (t, 3H, J=6.8 Hz). $^{13}$C NMR (CDCl$_3$, 100 MHz); δ (ppm): 159.5, 152.9, 140.8, 139.0, 129.2, 128.8, 128.2, 127.0, 121.1, 114.5, 112.2, 75.1, 59.5, 56.2, 55.1, 43.8, 43.1, 25.3, 12.0. HRMS (m/z): calcd for C$_{22}$H$_{29}$N$_2$O$_3$ [M+H]$^+$, 369.2178; found, 369.2160. IR (CH$_2$Cl$_2$; cm$^{-1}$): 3054, 2985, 1686, 1469, 1285, 738, 692 cm$^{-1}$.

Compound A17 $^1$H NMR (CDCl$_3$, 400 MHz); δ (ppm): 7.33-7.21 (m, 6H), 7.14 (m, 3H), 4.11 (m, 1H), 3.73 (d, 1H, J=6.8 Hz), 3.69 (d, 1H, J=5.9 Hz), 3.51 (m, 2H), 3.52 (d, 1H, J=1.9 Hz), 3.49 (d, 1H, J=1.9 Hz), 3.26 (m, 2H), 3.04 (dt, 1H, J=11.7, 5.9 Hz), 2.88 (m, 1H), 2.69 (dd, 1H, J=13.7, 4.9 Hz), 2.62 (dd, 1H, J=12.7, 7.8 Hz), 2.29 (s, 3H), 1.91 (m, 1H), 1.52 (m, 1H), 1.05 (t, 3H, J=6.8 Hz). $^{13}$C NMR (CDCl$_3$, 100 MHz); δ (ppm): 152.9, 138.9, 137.2, 136.9, 130.3, 129.9, 129.2, 128.2, 127.2, 125.6, 127.1, 74.9, 60.2, 58.0, 56.3, 43.8, 42.9, 25.2, 19.2, 12.0. HRMS (m/z): calcd for C$_{22}$H$_{29}$N$_2$O$_2$ [M+H]$^+$, 353.2229; found, 353.2221. IR (CH$_2$Cl$_2$; cm$^{-1}$): 3054, 2987, 1688, 1431, 1266, 747, 705 cm$^{-1}$.

Compound C1 $^1$H NMR (CDCl$_3$, 400 MHz); δ (ppm): 7.21-7.35 (m, 7H), 7.00 (t, 2H, J=8.8 Hz), 4.46 (m, 1H), 3.69 (d, 2H, J=13.7 Hz), 3.55 (d, 2H, J=13.7 Hz), 3.38 (t, 1H, J=8.8 Hz), 3.00 (dd, 1H, J=6.8, 8.8 Hz), 2.74 (s, 3H), 2.73 (dd, 1H, J=5.9, 13.7 Hz), 2.65 (dd, 1H, J=6.8, 13.7 Hz). $^{13}$C NMR (CDCl$_3$, 100 MHz); δ (ppm): 162.0 (d, C—F, J=244 Hz), 159.1, 138.8, 134.6, 130.4 (d, meta to F, $^3$J=6.1 Hz), 128.9, 128.4, 127.3, 115.2 (d, ortho to F, $^2$J=21.4 Hz), 71.4, 59.3, 58.7, 56.3, 50.3, 30.8.

Compound C2 $^1$H NMR (CDCl$_3$, 400 MHz); δ (ppm): 7.17-7.32 (m, 6H), 6.88 (m, 2H), 4.49 (m, 1H), 3.83 (d, 1H of AB system, J=12.7 Hz), 3.77 (d, 1H of AB system, J=12.7 Hz), 3.69 (d, 1H, J=13.7 Hz), 3.55 (d, 1H, J=13.7 Hz), 3.37 (m, 1H), 3.03 (dd, 1H, J=6.8, 8.8 Hz), 2.76 (dd, 1H, J=4.8, 13.7 Hz), 2.72 (s, 3H), 2.62 (dd, 1H, J=7.8, 13.7 Hz). $^{13}$C NMR (CDCl$_3$, 100 MHz); δ (ppm): 162.2 (dd, C$_2$—F, $^1$J=250.2, $^3$J=12.2 Hz), 161.4 (dd, C$_4$—F, $^1$J=250.2, $^3$J=12.2 Hz), 158.0, 138.6, 132.1 (m, C$_1$), 128.8, 128.3, 127.3, 127.4 (m, C$_6$), 111.1 (d, C$_5$, $^2$J=21.4 Hz), 103.7 (dd≈t, C$_3$, $^2$J=24.4 Hz), 71.3, 59.2, 56.2, 51.9, 50.2, 30.8.

Compound C3 $^1$H NMR (CDCl$_3$, 500 MHz); δ (ppm): 7.25-7.38 (m, 5H), 7.19 (m, 1H), 7.11 (m, 1H), 7.02-7.08 (m, 1H), 4.53 (m, 1H), 3.71 (d, 2H, J=13.7 Hz), 3.58 (d, 2H, J=13.7 Hz), 3.44 (dd, 1H, J=7.8, 8.8 Hz), 3.05 (dd, 1H, J=6.8, 8.8 Hz), 2.79 (s, 3H), 2.77 (dd, 1H, J=5.9, 13.7 Hz), 2.69 (dd, 1H, J=5.9, 13.7 Hz). $^{13}$C NMR (CDCl$_3$, 125 MHz); δ (ppm): 157.9, 150.4 (dd, C$_3$—F, $^1$J=247.8 Hz, $^2$J=12.8 Hz), 149.5 (dd, C$_4$—F, $^1$J=247.8 Hz, $^2$J=12.8 Hz), 138.4, 136.1 (m, C$_1$), 128.9, 128.5, 127.4, 124.5 (dd, C$_6$, $^3$J=6.0, $^4$J=3.4 Hz), 117.3 (d, $^2$J=17.1 Hz), 117.0 (d, $^2$J=17.1 Hz), 71.5, 59.2, 58.5, 56.4, 50.3, 30.9.

Compound C4 $^1$H NMR (CDCl$_3$, 400 MHz); δ (ppm): 7.42 (d, 2H, J=8.8 Hz), 7.19 (d, 2H, J=8.8 Hz), 7.22-7.33 (m, 5H), 3.68 (d, 1H, J=13.7 Hz), 3.67 (d, 1H, J=13.7 Hz), 3.55 (d, 1H, J=13.7 Hz), 3.54 (d, 1H, J=13.7 Hz), 3.38 (t, 1H, J=8.8 Hz), 3.00 (m, 1H), 2.74 (s, 3H), 2.73 (dd, 1H, J=5.9, 13.7 Hz), 2.65 (dd, 1H, J=5.9, 13.7 Hz). $^{13}$C NMR (CDCl$_3$, 100 MHz); δ (ppm): 157.9, 138.6, 138.0, 131.4, 130.5, 128.8, 128.3, 127.3, 120.9, 71.4, 59.3, 58.7, 56.3, 50.2, 30.8.

Compound C5 $^1$H NMR (CDCl$_3$, 400 MHz); δ (ppm): 7.52 (d, 1H, J=7.8 Hz), 7.47 (d, 1H, J=7.8 Hz), 7.19-7.32 (m, 6H), 7.10 (dd, 1H, J=1.95, 7.8 Hz), 4.43 (m, 1H), 3.83 (d, 1H, J=13.7 Hz), 3.72 (d, 1H, J=13.7 Hz), 3.71 (d, 1H, J=13.7 Hz), 3.60 (d, 1H, J=13.7 Hz), 3.34 (t, 1H, J=8.8 Hz), 2.96 (dd, 1H, J=5.9, 8.8 Hz), 2.78 (dd, 1H, J=5.9, 13.7 Hz), 2.69 (s, 3H), 2.66 (dd, 1H, J=6.8, 13.7 Hz). $^{13}$C NMR (CDCl$_3$, 100 MHz); δ (ppm): 157.9, 138.5, 137.9, 132.8, 131.1, 129.0, 128.7, 128.2, 127.3, 127.2, 124.5, 71.1, 59.4, 59.1, 56.4, 50.3, 30.7.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent, patent application and printed publication referred to above is incorporated herein by reference in toto to the fullest extent permitted as a matter of law.

This invention is susceptible to considerable variation in its practice. Therefore, the foregoing description is not intended to limit, and should not be construed as limiting, the invention to the particular exemplifications presented hereinabove.

The invention claimed is:

1. A compound which is a 1,3-oxazinan-2-one of formula (I)

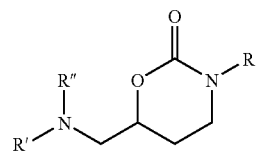

wherein

R is a hydrocarbyl group, a heterocyclic group, a hydrocarbyl group having at least one substituent, or a heterocyclic group having at least one substituent, wherein the substituent on the hydrocarbyl group or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms; and R' is an alkyl group, an aryl group, a methylaryl group, an alkyl carbonyl group, an aryl carbonyl group, a hydrocarbylamido group, an alkyl sulfonyl group, an aryl sulfonyl group, an alkyl sulfonamoyl group, an aryl sulfonamonyl group, a heterocyclic group, a heterocyclic group having at least one substituent, or an aryl group or methylaryl group having at least one substituent thereon, where the substituent on the heterocyclic group, aryl group, or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, and R" is a methylnaphthyl group, or an aryl group or methylaryl group having at least one substituent thereon, where the substituent on the aryl group or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms.

2. A compound as in claim 1 wherein R is an alkyl or aryl group.

3. A compound as in claim 1 wherein R" is an aryl group or methylaryl group having at least one substituent thereon.

4. A compound as in claim 1 wherein R" is a benzyl or methylnaphthyl group having at least one substituent thereon.

5. A compound as in claim 1 wherein R" is an aryl group or methylaryl group having at least one substituent thereon, and wherein the substituent is in an ortho position.

6. A compound as in claim 5 wherein the substituent is a chloro group, a bromo group, or a methyl group.

7. A compound as in claim 1 wherein R is an alkyl or aryl group, and wherein R" is an aryl group or methylaryl group having at least one substituent thereon.

8. A compound as in claim 7 wherein R" is a benzyl or methylnaphthyl group having at least one substituent thereon.

9. A compound as in claim 8 wherein the substituent is in an ortho position.

10. A compound as in claim 8 wherein the substituent is a chloro group, a bromo group, or a methyl group.

11. A pharmaceutically acceptable salt of a 1,3-oxazinan-2-one compound of claim 1.

12. A method for inhibiting bacterial growth, which method comprises bringing into contact the 1,3-oxazinan-2-one compound of claim 1 and bacteria.

13. A process for preparing the 1,3-oxazinan-2-one compound of formula (I) of claim 1, which process comprises contacting i) a 1,3-oxazinan-2-one compound of the formula

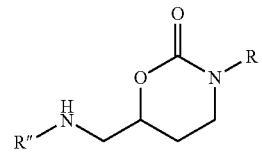

wherein R is a hydrocarbyl group, a heterocyclic group, a hydrocarbyl group having at least one substituent, or a heterocyclic group having at least one substituent, wherein the substituent on the hydrocarbyl group or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, and wherein R" is hydrogen, an alkyl group, an aryl group, a methylaryl group, an alkyl carbonyl group, an aryl carbonyl group, a hydrocarbylamido group, an alkyl sulfonyl group, an aryl sulfonyl group, an alkyl sulfonamoyl group, an aryl sulfonamonyl group, a heterocyclic group, a heterocyclic group having at least one substituent thereon, or an aryl group or methylaryl group having at least one substituent, where the substituent on the heterocyclic group, aryl group, or methylaryl group is selected from the group consisting of a heterocycle, an azo group, a cyano group, a nitro group, a fluoro group, a chloro group, a bromo group, an alkoxy group having up to 15 carbon atoms, and a hydrocarbyl group having up to 15 carbon atoms; and ii) a compound of the formula R'L, wherein R' is hydrogen, an alkyl group, an aryl group, a methylaryl group, an alkyl carbonyl group, an aryl carbonyl group, a hydrocarbylamido group, an alkyl sulfonyl group, an aryl sulfonyl group, an alkyl sulfonamoyl group, an aryl sulfonamonyl group, a heterocyclic group, a heterocyclic group having at least one substituent, or an aryl group or methylaryl group having at least one substituent thereon, where the substituent on the heterocyclic group, aryl group, or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms, and wherein L is a leaving group.

14. A process as in claim 13 wherein R is an alkyl group or an aryl group.

15. A process as in claim 13 wherein R" is an aryl group, a methylaryl group, or an aryl group or methylaryl group having at least one substituent thereon.

16. A process as in claim 13 wherein R" is a benzyl group, a methylnaphthyl group, or a benzyl or methylnaphthyl group having at least one substituent thereon.

17. A process as in claim 13 wherein R" is an aryl group or methylaryl group having at least one substituent thereon, and wherein the substituent is in an ortho position.

18. A process as in claim 17 wherein the substituent is a chloro group, a bromo group, or a methyl group.

19. A process as in claim 13 wherein R is an alkyl group or an aryl group, and wherein R" is an aryl group, a methylaryl group, or an aryl group or methylaryl group having at least one substituent thereon.

20. A process as in claim 19 wherein R" is an aryl group or methylaryl group having at least one substituent thereon, and wherein the substituent is in an ortho position.

21. A process as in claim 19 wherein R" is an aryl group or methylaryl group having at least one substituent thereon, and wherein the substituent is a chloro group, a bromo group, or a methyl group.

22. A process as in claim 13 wherein L is a sulfonate or a halide.

23. A process as in claim 13 wherein L is a halide, and wherein the halide is chloride or bromide.

24. A pharmaceutically acceptable salt of 1,3-oxazinan-2-one compound of formula (II)

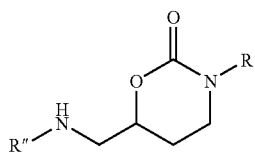

(II)

wherein
R is a hydrocarbyl group, a heterocyclic group, a hydrocarbyl group having at least one substituent, or a heterocyclic group having at least one substituent, wherein the substituent on the hydrocarbyl group or heterocyclic group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms; and R" is an alkyl group, an aryl group, a methylaryl group, an alkyl carbonyl group, an aryl carbonyl group, a hydrocarbylamido group, an alkyl sulfonyl group, an and sulfonyl group, an alkyl sulfonamoyl group, an and sulfonamonyl group, a heterocyclic group, a heterocyclic group having at least one substituent, or an aryl group or methylaryl group having at least one substituent thereon, where the substituent on the heterocyclic group, aryl group, or methylaryl group is selected from the group consisting of a heterocyclic group, an azo group, a cyano group, a nitro group, a fluoro group, a chloro group, a bromo group, an alkoxy group having up to 15 carbon atoms, and a hydrocarbyl group having up to 15 carbon atoms.

25. A pharmaceutically acceptable salt as in claim 24 wherein the 1,3-oxazinan-2-one compound either has the formula

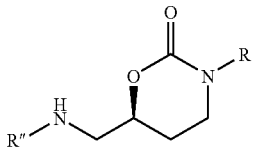

or is the enantiomer of this formula.

26. A compound as in claim 1 wherein the 1,3-oxazinan-2-one compound of formula (I) either has the formula

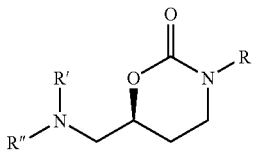

or is the enantiomer of this formula.

27. A process as in claim 13 wherein the 1,3-oxazinan-2-one compound in i) either has the formula

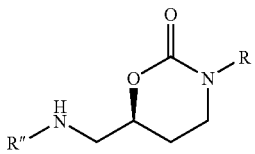

or is the enantiomer of this formula.

* * * * *

UNITED STATES PATENT AND TRADEMARK OFFICE
CERTIFICATE OF CORRECTION

PATENT NO.       : 7,700,590 B2
APPLICATION NO.  : 12/278871
DATED            : April 20, 2010
INVENTOR(S)      : Guijun Wang It is certified that error appears in the above-identified patent and that said Letters Patent is hereby corrected as shown below:

Column 23, lines 36-37, reads "an and sulfonyl" and should read -- an aryl sulfonyl --

Column 23, lines 37-38, reads "an and sulfonamonyl" and should read -- an aryl sulfonamonyl --

Signed and Sealed this

First Day of June, 2010

David J. Kappos
*Director of the United States Patent and Trademark Office*